US007771941B2

(12) United States Patent
Stroot et al.

(10) Patent No.: US 7,771,941 B2
(45) Date of Patent: *Aug. 10, 2010

(54) METHOD FOR DETERMINING THE SPECIFIC GROWTH RATE OF DISTINCT MICROBIAL POPULATIONS IN A NON-HOMOGENEOUS SYSTEM

(75) Inventors: Peter George Stroot, Lutz, FL (US); Matthew Raymond Cutter, Tampa, FL (US); Samuel James DuPont, Jr., Tampa, FL (US)

(73) Assignee: University of South Florida, Tampa, FL (US)

( * ) Notice: Subject to any disclaimer, the term of this patent is extended or adjusted under 35 U.S.C. 154(b) by 80 days.

This patent is subject to a terminal disclaimer.

(21) Appl. No.: 11/821,946

(22) Filed: Jun. 25, 2007

(65) Prior Publication Data

US 2008/0009011 A1 Jan. 10, 2008

Related U.S. Application Data

(60) Provisional application No. 60/815,997, filed on Jun. 23, 2006.

(51) Int. Cl.
*C12Q 1/68* (2006.01)
(52) U.S. Cl. ........................................................ 435/6
(58) Field of Classification Search ........................ None
See application file for complete search history.

(56) References Cited

U.S. PATENT DOCUMENTS

| 5,712,095 | A | 1/1998 | Britschgi et al. |
| 5,726,021 | A | 3/1998 | Britschgi et al. |
| 5,770,373 | A | 6/1998 | Britschgi et al. |
| 6,699,670 | B2 | 3/2004 | Rothman et al. |
| 6,808,879 | B1 | 10/2004 | Guillot et al. |
| 2004/0072242 | A1 | 4/2004 | Hunter et al. |
| 2006/0105339 | A1 | 5/2006 | Hellerstein |

OTHER PUBLICATIONS

Ahern, The Scientist 9(15), 20 (1995).*
U.S. Appl. No. 11/521,765, filed Sep. 16, 2006, Stroot et al.
Adamczyk et al., "The Isotope Array, a New Tool That Employs Substrate-Mediated Labeling of rRNA for Determination of Microbial Community Structure and Function" *Appl. And Environ. Microbiol.*, Nov. 2003, pp. 6875-6887, vol. 69, No. 11.
Al-Qadiri et al., "Rapid Detection and Identification of *Pseudomonas aeruginosa* and *Escherichia coli* as Pure and Mixed Cultures in Bottled Drinking Water Using Fourier Transform Infrared Spectroscopy and Multivariate Analysis." *J Agric. Food Chem.*, 2006, pp. 5749-5754, vol. 54.
Amann et al., "Monitoring the community structure of wastewater treatment plants: a comparison of old and new techniques" *REMS Microbiology Ecology*, 1998, pp. 205-215, vol. 25, No. 3.
Bottari et al., "Application of FISH technology for microbiological analysis: current state and prospects" *Appl. Microbiol. Biotechnol.*, 2006, pp. 485-494, vol. 73.
Bremer et al., "Modulation of chemical composition and other parameters of the cell by growth rate" *Escherichia coli and Salmonella*, F.C. Neidhardt, et al., Eds., 1996, ASM Press: Washington, D.C.
Cangelosi et al., "Detection of Stable Pre-rRNA in Toxigenic *Pseudo-nitzschia* Species" *Applied and Environmental Microbiology*, Dec. 1997, pp, 4859-4865, vol. 63, No. 12.
Cangelosi et al., "Depletion of Pre-16S rRNA in Starved *Escherichia coli* Cells" *J. of Bacteriology*, Jul. 1997, pp. 4457-4463, vol. 179, No. 14.
Dar et al., Analysis of Diversity and Activity of Sulfate-Reducing Bacterial Communities in Sulfidogenic Bioreactors Using 16S rRNA and dsrB Genes as Molecular Markers *Applied and Environmental Microbiology*, Jan. 2007, pp. 594-604, vol. 73, No. 2.
Delong et al., "Phylogenetic Stains: Ribosomal RNA—Based Proves for the Identification of Single Cells" *Science*, Mar. 10, 1989, pp. 1360-1363, vol. 243, No. 4896.
Dennis et al., "Monitoring Gene Expression in Mixed Microbial Communities by Using DNA Microarrays." *Applied and Environmental Microbiology*, Feb. 2003, pp. 769-778 vol. 69, No. 2.
Fogel et al., "Temperature Gradient Chamber for Relative Growth Rate Analysis of Yeast" *Analytical Biochemistry*, 1998, pp. 80-84, vol. 260, No. 1.
Haugen et al., "Application of gas-sensor array technology for detection and monitoring of growth of spoilage bacteria in milk: A model study" *Analytica Chimica Acta*, 2006, pp. 10-16, vol. 565.

(Continued)

*Primary Examiner*—James Martinell
(74) *Attorney, Agent, or Firm*—Saliwanchik, Lloyd & Saliwanchik

(57) ABSTRACT

The present invention pertains to a molecular biology-based method and kit for measuring the specific growth rate (or cell doubling time) of distinct microbial populations. The method and kit can be used to analyze mixed culture samples that have been exposed to chloramphenicol or other protein synthesis inhibitors for defined times. In a preferred embodiment, the method of the invention (also referred to herein as FISH-RiboSyn) is an in situ method that utilizes fluorescence in situ hybridization (FISH) with probes that target: (1) the 5' or 3' end of precursor 16S rRNA; or (2) the interior region of both precursor 16S rRNA and mature 16S rRNA. Images can be captured for a defined exposure time and the average fluorescent intensity for individual cells can be determined. The rate of increase of the whole cell fluorescent intensity is used to determine the specific growth rate. The method of the invention can be attractive for rapidly measuring the specific growth rate (or cell doubling time) of distinct microbial populations within a mixed culture in industries such as environmental systems (water and wastewater treatment systems), bioremediation (optimization of conditions for microbial growth), public health (identification of rapidly growing infectious microbes), and homeland security (identification of rapidly growing bioterrorism agents).

21 Claims, 18 Drawing Sheets
(6 of 18 Drawing Sheet(s) Filed in Color)

OTHER PUBLICATIONS

Hugenholtz, "Exploring prokaryotic diversity in the genomic era" *Genome Biol.*, Jan. 2002, pp. reviews0003.1-0003.8, vol. 3, No. 2.

Kaewpipat et al., "Microbial population dynamics in laboratory-scale activated sludge reactors" *Water Sci. Technol.*, 2002, pp. 19-27, vol. 46, No. 1-2.

Kerkhof et al., "Comparison of Nucleic Acid Hybridization and Fluorometry for Measurement of the Relationship between RNA/DNA Ratio and Growth Rate in a Marine Bacterium" *Applied and Environmental Microbiology*, May 1993, pp. 1303-1309, vol. 59, No. 5.

Kostic et al., "A microbial diagnostic microarray technique for the sensitive detection and identification of pathogenic bacteria in a background of nonpathogens." *Analytical Biochemistry*, 2007, pp. 244-254, vol. 360.

Kreuzinger et al., "Molecular biological methods (DGGE) as a tool to investigate nitrification inhibition in wastewater treatment" *Water Sci. Technol.*, 2003, pp. 165-172, vol. 47, No. 11.

Licht et al., "Inhibition of *Escherichia coli* precursor-16S rRNA processing by mouse intestinal contents" *Environmental Microbiology*, 1999, pp. 23-32, vol. 1, No. 1.

Lin et al, "Using a Resequencing Microarray as a Multiple Respiratory Pathogen Detection Assay." *Journal of Clinical Microbiology*, Feb. 2007, pp. 443-452, vol. 45, No. 2.

Liu "Determination of the Microbial Diversity of Anaerobic-Aerobic Activated Sludge by a Novel Molecular Biological Technique" *Water Sci. Technol.*, 1998, pp. 417-422, vol. 37, No. 4-5.

Loy et al., "probeBase: an online resource for rRNA-targeted oligonucleotide probes" *Nucleic Acids Res.*, 2003, pp. 514-516, vol. 31, No. 1.

Merlin et al., "Analysis of Establishment Phase Replication of the Plasmid ColE1" *J. Mol. Biol.*, Mar. 1993, pp. 137-150, vol. 230, No. 1.

Metherell et al., "Rapid, sensitive, microbial detection by gene amplification using restriction endonuclease target sequences" *Molecular and Cellular Probes*, 1997, pp. 297-308, vol. 11.

Molin et al., "Application of molecular tools for in situ monitoring of bacterial growth activity" *Environmental Microbiology*, 2003, pp. 383-391, vol. 1, No. 5.

Nielsen et al., "Quantification of cell-specific substrate uptake by probe-defined bacteria under in situ conditions by microautoradiography and fluorescence in situ hybridization" 2003, pp. 202-211, vol. 5, No. 3.

Oerther et al., "Monitoring Precursor 16S rRNAs of *Acinetobacter* spp. In Activated Sludge Wastewater Treatment Systems" *Appl. And Environ. Microbiol.*, May 2000, pp. 2154-2165, vol. 66, No. 5.

Ouverney et al., "Combined Microautoradiography-16S rRNA Probe Technique for Determination of Radioisotope Uptake by Specific Microbial Cell Types In Situ." *Applied and Environmental Microbiology*, Apr. 1999, pp. 1746-1752, vol. 65, No. 4.

Poulsen et al., "Use of rRNA Fluorescence in Situ Hybridization for Measuring the Activity of Single Cells in Young and Established Biofilms" *Appl. Environ. Microbiol.*, 1993, pp. 1354-1360, vol. 59, No. 5.

Schloss et al., "Quantifying Bacterial Population Dynamics in Compost Using 16S rRNA Gene Probes" *Appl. Microbiol. Biotechnol.*, 2005, pp. 457-463, vol. 66.

Schramm et al., "Identification and Activities In Situ of *Nitrosospira* and *Nitrospira* spp. As Dominant Populations in a Nitrifying Fluidized Bed Reactor" *Appl. Environ. Microbiol.*, 1998, pp. 3480-3485, vol. 64, No. 9.

Srivastava et al., "Mechanism and Regulation of Bacterial Ribosomal RNA" *Annual Review of Microbiology*, 1990, pp. 105-129, vol. 44.

Starks et al., "Use of a marker plasmid to examine differential rates of growth and death between clinical and environmental strains of *Vibrio vulnificus* in experimentally infected mice." *Molecular Microbiology*, 2006, pp. 310-323, vol. 61, No. 2.

Tomlins et al., "Precursor Ribosomal Ribonucleic Acid and Ribosome Accumulation in Vivo During the Recovery of *Salmonella typhimurium* from Thermal Injury" *J. Bacteriol.*, 1971, pp. 134-142, vol. 107, No. 1.

Woese et al., "Phylogenetic structure of the prokaryotic domain: The primary kingdoms" *Proc. Natl. Acad. Sci. USA*, Nov. 1977, pp. 5088-5090, vol. 74, No. 11.

Woese et al., "Toward a Natural System of Organisms: Proposal for the Domains Archaea, Bacteria, and Eucarya" *Proc. Natl. Acad. Sci. USA*, Jun. 1990, pp. 4576-4579, vol. 87, No. 12.

Yang et al., "Specific Detection of *Dehalococcoides* Species by Fluorescence In Situ Hybridization with 16S rRNA-Targeted Oligonucleotide Probes" *Applied and Environmental Microbiology*, May 2003, pp. 2879-2883, vol. 69, No. 5.

Felske, A. et al. "Quantification of 16S rRNAs in Complex Bacterial Communities by Multiple Competitive Reverse Transcription-PCR in Temperature Gradient Gel Electrophoresis Fingerprints" *Appl. And Environ. Microbiol.*, Nov. 1998, pp. 4581-4587, vol. 64, No. 11.

\* cited by examiner

METHOD FOR DETERMINING THE SPECIFIC GROWTH RATE OF DISTINCT MICROBIAL POPULATIONS IN A NON-HOMOGENEOUS SYSTEM

CROSS-REFERENCE TO RELATED APPLICATION

The present application claims the benefit of U.S. Provisional Application Ser. No. 60/815,997, filed Jun. 23, 2006, which is hereby incorporated by reference herein in its entirety, including any figures, tables, nucleic acid sequences, amino acid sequences, and drawings.

BACKGROUND OF THE INVENTION

Before the 1970s, the phylogeny of the prokaryotes was based on crude comparisons of morphology and pattern of substrate utilization and was largely ignored due to the presumed simplicity of the organisms. Carl Woese used a different strategy to tackle prokaryotic phylogeny. He focused on sequence comparisons of the ribosome, a biomolecule found in all life forms. The ribosome is an essential macromolecule that is involved in the translation of messenger RNA into proteins. Woese argued that since protein synthesis is an essential function for life, the ribosome could not withstand major sequence changes or life would cease. He then targeted one molecule, the 16S rRNA of prokaryotes and the analogous 18S rRNA for eukaryotes, and did comparisons by sequence analysis (Woese, C. R. and G. E. Fox *Proc. Natl. Acad. Sci. USA*, 1977, 74:5088-5090). A new phylogeny of all life was discovered and to his surprise (and other biologists), the old phylogeny of eukaryotes and prokaryotes was discarded for a three-kingdom version that included bacteria, archaea, and eucarya (shown in FIG. 1). Over time, most biologists have accepted this paradigm shift. To date, 35 bacteria phyla and 18 archaea phyla were identified, despite only having 30 cultivatable representatives for both (Hugenholtz, P. *Genome Biol*, 2002, 3(2):0003). With the discovery of a robust bacterial phylogeny by Woese, molecular biology-based methods have slowly replaced traditional methods in the study of microbial populations in environmental samples (Woese, C. R. et al. *Proc. Natl. Acad. Sci. USA*, 1990, 87:4576-4579). These molecular biology based techniques rely on the 16S rRNA, the biomolecule used by Woese to determine the phylogeny of bacteria and archaea. Over the past twenty years, molecular biology tool development has progressed from determining community structure to community function.

Specific microbial populations have a unique sequence signature within the 16S or 18S rRNA. Norman Pace recognized that specific microbial populations have signature sequences within the 16S or 18S rRNA that can be targeted by molecular biology based methods. Pace's group was the first to demonstrate the use of fluorescence in situ hybridizations with an oligonucleotide probe that is complementary to these signature sequences (DeLong, E. F. et al. *Science*, 1989, 243 (4896):1360-3). With this approach, they were able to identify and enumerate microbes within a mixed culture sample at various phylogenetic levels. Today, probes and their hybridization characteristics for specific microbial populations are commercially available through convenient websites (Loy, A. et al. *Nucleic Acids Res*, 2003, 31(1):514-516). For example, the sequence, hybridization conditions, and other characteristics of an oligonucleotide probe that targets the 16S rRNA of the genus *Nitrospira* (ProbeBase accession number pB-00627) are as follows: specificity: *Nitrospira* spp.; target molecule: 16S rRNA; position: 447-464; sequence: 5'-GGTTTCCCGTTCCATCTT-3' (SEQ ID NO:1); length: 18 nt; G+C content: 50%; Tm: 48° C.; delta Gs: $\Delta G_1$: −22.03; $\Delta G_2$: 1.41; $\Delta G_{12}$: −21.96; MW: 5406 g/mol; formamide: 30%; (Schramm, A. et al. *Appl. Environ. Microbiol.*, 1998, 64:3480-3485; information provided by ProbeBase, an online database of probes at the Department of Microbial Ecology, University of Vienna).

Molecular biology-based methods have now replaced classical methods in the study of microbes. Since Pace's demonstration of FISH, molecular biology-based methods have been developed to investigate microbial populations in mixed cultures, such as bioreactors and environmental samples. As shown by FIG. 2, three classes of molecular biology-based methods have been developed to identify, enumerate, and determine the function of specific microbial populations. A fourth class of molecular biology based methods provides a measure of the diversity. All of these molecular biology-based methods draw on the sequence information of the 16S rRNA.

The investigation of the microbiology of mixed culture samples involves determining the identity and abundance of microbes present (microbial community structure) and their role in the mixed culture sample (microbial community function). Traditionally, light microscopy or culture-based methods were used to characterize the microbial structure of mixed culture samples. More recently, new tools that draw on molecular biology and a new view of the phylogeny of life have been developed to identity bacteria and determine their function.

Molecular biology tools have been used to determine community structure and function. The first wave of molecular biology tools identify and enumerate specific microbial populations in environmental systems. Recently, Amann et al. (Amann, R. et al. *FEMS Microbiology Ecology*, 1998, 25:205-215) reviewed molecular biology based techniques for identifying and enumerating bacterial populations and these are summarized below. For specific microbial populations where the 16S rRNA sequence information is available, tools are available to identify individual cells in situ (fluorescence in situ hybridizations or FISH) (DeLong, E. F. et al. *Science*, 1989, 243(4896):1360-3) or provide estimates of abundance for a microbial population ex situ (membrane hybridizations). For uncharacterized samples, researchers use DNA amplification by polymerase chain reaction (PCR) that targets large phylogenetic groups combined with conventional cloning methods to identify the different types of microbes present. Finally, fingerprinting methods such as terminal restriction length polymorphism (T-RFLP) and denaturing gradient gel electrophoresis (DGGE) characterize the diversity and evenness of environmental samples (Liu, W. T. *Water Science and Technology*, 1998, 37(4-5): 417-422; Kaewpipat, K. and C. P. Grady, Jr. *Water Sci Technol*, 2002, 46(1-2):19-27; Kreuzinger, N. et al. *Water Sci Technol*, 2003, 47(11):165-72).

The second wave of molecular biology tools determined the function of specific microbial populations in situ or ex situ. FISH is combined with microautoradiography (FISH-MAR) to provide a method that identifies microbes that metabolize specific compounds. With FISH-MAR, environmental samples are exposed to radio-labeled substrates. In some cases, the rate of substrate uptake has been reported (Nielsen, J. L. et al. *Environ Microbiol*, 2003, 5(3):202-11). FISH-MAR is a difficult method to master, which limits its acceptance as a second wave tool. An ex situ method called Isotope Array is based on the same principle as FISH-MAR, but membrane hybridizations are used to identify the dominant microbial population linked to substrate uptake (Adamczyk, J. et al. *Appl Environ Microbiol*, 2003, 69(11):6875-87).

Molecular biology tools for examining the growth activity of microbial communities in environmental samples are being utilized. Three strategies are currently used for determining the growth activity of the microbial members in biological reactor systems. The simplest strategy involves detecting and enumerating the bacteria that are only able to carry out certain metabolic functions. In this case, a simple identification and enumeration by the methods used for microbial structure analysis are needed. The second strategy determines the abundance of genes or mRNA present in a sample that is specific for an enzyme in the specific metabolic pathway of interest. The identification of the microbes containing these genes or mRNA is not always possible, since these biomolecules are not phylogenetic markers and are present at low cellular levels. The third strategy determines whether the microbes of interest are growing. With this strategy, the measurement of the rRNA present in the cells is required. Membrane hybridizations have been used by researchers as evidence that a bacterial population is active when their relative 16S rRNA levels increase. Detection of increased ribosome synthesis has been used to determine when bacterial populations or individual cells of a bacterial population are actively growing. These methods and others involving genetically modified organisms have been reviewed (Molin, S, and M. Givskov *Environmental Microbiology*, 1999, 1(5):383-391).

For the past 50 years, scientists have been measuring the specific growth rate of pure cultures by using spectrophotometers (see FIGS. 3A and 3B). Over time, the optical density is measured for a defined wavelength and compared to a blank that contains sterile broth media. With a simple spreadsheet, the specific growth rate of the culture is determined by examination of the rate of increase of the optical density.

The specific rate of ribosome synthesis (or ribosome doubling time) is identical to the specific growth rate (or cell doubling time) of the culture. During log growth, cells are growing at a constant specific growth rate, which also means they have a defined and constant doubling time. Similarly, the ribosome doubling time has to be identical to the cell doubling time, which is depicted in FIG. 4.

During the 1960's, researchers first reported that the macromolecular composition of pure cultures was dependent on the growth rate (Maaløe, O. and N. O. Kjeldgaard, "Control of Macromolecular Synthesis; a study of DNA, RNA, and protein synthesis in bacteria" 1966, New York: W. A. Benjamin, p. 284). The relationship between the macromolecular composition and growth phase of *E. coli* strain B/r is shown in Table I (Bremer, H. and P. P. Dennis, "Modulation of chemical composition and other parameters of the cell by growth rate" in *Escherichia coli* and *Salmonella*, F. C. Neidhardt, et al., Editors; 1996, ASM Press: Washington, D.C.). Two basic descriptors of ribosome synthesis, rRNA transcription and cellular ribosome levels, are also included. The rRNA transcription is reported as the fraction of total transcription.

TABLE 1

Comparison of specific growth rate, rRNA transcription, and macromolecular composition of *E. coli* strain B/r.

| Specific Growth Rate | rRNA transcription | Ribosomes per cell | Composition % | | |
|---|---|---|---|---|---|
| $hr^{-1}$ | % | — | RNA | DNA | Protein |
| 0.6 | 35 | 6,800 | 14 | 5 | 68 |
| 2.5 | 73 | 72,000 | 24 | 2 | 52 |

An approximately 10-fold increase in ribosome level is observed when *E. coli* increases its specific growth rate from $0.6\,hr^{-1}$ to $2.5\,hr^{-1}$. During rapid growth, over 50% of the total RNA produced in *E. coli* is ribosomal RNA (rRNA), which is remarkable given that there are only 14 promoters associated with the seven rrn operons compared to 2,000 total promoters available (Gourse, R. L. and M. Nomura, "*Prokaryotic rRNA gene expression*, in *Ribosomal RNA: structure, evolution, processing, and function in protein biosynthesis*" R. A. Zimmermann and A. E. Dahlberg, Editors. 1996, CRC Press, Inc.: Boca Raton. p. 373-394). The largest macromolecule fraction for all growth rates is protein. As the growth rate increases, the RNA content increases and protein content decreases. This is caused by the increase of ribosome levels or stable RNA. Bremer and Dennis (Bremer, H. and P. P. Dennis, "Modulation of chemical composition and other parameters of the cell by growth rate" in *Escherichia coli* and *Salmonella*, F. C. Neidhardt, et al., Editors; 1996, ASM Press: Washington, D.C.) developed a growth equation for *E. coli* that was a function of constant ribosome concentration (number of ribosomes per protein) and activity (protein synthesis rate per ribosome).

Some researchers have used fluorescence in situ hybridizations with probes that target the ribosomes in cells and reported that faster growing cells have higher levels of ribosomes based on fluorescent intensity (DeLong, E. F. et al. *Science*, 1989, 243(4896):1360-3; Poulsen, L. K. et al. *Appl Environ Microbiol*, 1993, 59(5):1354-60). However, this approach was discarded as a method for measuring the specific growth rate (or cell doubling time), since cells maintain high levels of ribosomes during stationary phase which would be misinterpreted as rapidly growing cells.

Central to microbial growth is ribosome synthesis, the production of functional ribosomes. Currently, the ribosome synthesis model of *Escherichia coli* is the most complete, best understood, and hypothesized to describe ribosome synthesis for Bacteria. A basic review of *E. coli* ribosome synthesis is provided below, however several detailed reviews of *E. coli* ribosome synthesis are available (Gourse, R. L. and M. Nomura, "*Prokaryotic rRNA gene expression, in Ribosomal RNA. structure, evolution, processing, and function in protein biosynthesis*" R. A. Zimmermann and A. E. Dahlberg, Editors. 1996, CRC Press, Inc.: Boca Raton. p. 373-394; Jemiolo, D. K. "Processing of Prokaryotic ribosomal RNA" in *Ribosomal RNA: structure, evolution, processing, and function in protein biosynthesis*, R. A. Zimmermann and A. E. Dahlberg, Editors; 1996, CRC Press, Inc.: Boca Raton, p. 453-468; Srivastava, A. K. and D. Schlessinger *Annual Review of Microbiology*, 1990, 44:105-129). A schematic of ribosome synthesis in bacteria is shown in FIG. 5. Expression of the rrn operon produces a polycistronic transcript consisting of the three rRNAs: 5S, 16S, and 23S. Two processing steps are required to produce mature rRNAs for ribosome assembly. In the primary processing step, RNaseIII cleaves the polycistronic transcript resulting in three precursor rRNAs: precursor 5S (pre5S), precursor 16S (pre16S), and precursor 23S (pre23S). A secondary processing step removes unnecessary RNA from both 5' and 3' ends of the precursor rRNAs before ribosome assembly. This secondary processing step is slower than the primary processing step, which results in an intracellular pool of precursor rRNAs.

Chloramphenicol disrupts ribosome synthesis. As shown in FIG. 6 and FIG. 7, chloramphenicol inhibits the secondary processing of precursor 16S rRNA, but does not inhibit the production of precursor 16S rRNA (Tomlins, R. I. and Z. J. Ordal *J Bacteriol*, 1971, 107(1):134-42). Cangelosi and Brabant (Cangelosi, G. A. and W. H. Brabant *Journal of Bacteriology*, 1997, 179(14):4457-4463) used a reverse transcription method to measure the level of precursor 16S rRNA in cells of *E. coli* that were exposed to chloramphenicol. Their results suggested a marked difference in the rate of the buildup of the pre16S rRNA in growing and non-growing cells that were exposed to chloramphenicol. Chloramphenicol treated *E. coli* cells were also reported to have substantially higher level of pre16S rRNA than normally observed for LB cultures (Licht, T. R. et al. *Environmental Microbiology*, 1999, 1(1):23-32).

FIG. 7 is a simplified example of a cell in log growth phase that is exposed to chloramphenicol. In this figure, the initial level of pre16S rRNA is zero compared to the level of 16S rRNA (80,000), which represents ribosomes. After exposure to chloramphenicol, the level of 16S rRNA remains constant, while the pre16S rRNA increases to 40,000 after 15 minutes and 80,000 after 30 minutes. For non-growing cells (e.g., in stationary phase) exposed to chloramphenicol, the level of pre16S rRNA and 16S rRNA will remain constant.

U.S. Pat. Nos. 5,770,373; 5,726,021; and 5,712,095, which are each incorporated by reference herein in its entirety, describe methods for identifying chloramphenicol-resistant strains of mycobacteria, and the typical response of ribosome synthesis to chloramphenicol. U.S. Patent Application Publication No. 200400772242, which is incorporated herein by reference in its entirety, describes a method for detecting, enumerating and/or identifying microorganisms in a sample. U.S. Patent Application Publication No. 20060105339, which is incorporated herein by reference in its entirety, describes a method for measuring the rates of replication and death of microbial infectious agents within an infected host organism. A molecular biology-based method that measures the specific growth rate (or cell doubling time) of distinct microbial populations in a mixed culture has not previously been reported.

The identification of microbial populations through the use of molecular biology-based methods has been a boon for researchers in the areas of environmental science and engineering, microbial ecology, drug discovery, public health, homeland security, etc. A molecular biology-based tool that measures the specific growth rate of distinct microbial populations would be of great interest to scientists and engineers that share an interest in determining how fast microbes are growing. Industries that may benefit include, but are not limited to, environmental systems (water and wastewater treatment systems), bioremediation (optimization of conditions for microbial growth), public health (identification of rapidly growing infectious microbes), and homeland security (identification of rapidly growing bioterrorism agents).

BRIEF SUMMARY OF THE INVENTION

The present invention pertains to a molecular biology-based method and kit for measuring the specific growth rate (or cell doubling time) of distinct microbial populations. The method and kit can be used to analyze mixed culture samples that have been exposed to chloramphenicol or other protein synthesis inhibitor for defined times. Chloramphenicol disrupts ribosome synthesis, which causes a buildup of the level of precursor 16S rRNA within the cells. Distinct microbial populations can be targeted, because of signature sequences present in precursor 16S rRNA. The method measures the rate of increase of the precursor 16S rRNA within the cells, which is used to measure the specific growth rate (or cell doubling time) of a distinct microbial population. This link between the specific rate of ribosome synthesis (or ribosome doubling time) and specific growth rate (or cell doubling time) for a cell is true for log growth and stationary phase, where the specific growth rate is zero (or cell doubling time is infinity).

In preferred embodiments, the method of the invention comprises:

1) exposing a non-homogeneous system, such as a mixed culture sample, to chloramphenicol, or other protein synthesis inhibitor, in the existing environmental conditions;

2) collecting samples over time (preferably, at defined times) from the non-homogeneous system that is exposed to the protein synthesis inhibitor; and 3) analyzing the collected samples by a molecular biology-based method that will measure the rate of pre16S rRNA buildup (preferably, the rate of pre16S rRNA buildup can be measured in situ with FISH).

The specific growth rate (or cell doubling time) for a distinct microbial population can be determined by its rate of pre16S rRNA buildup. Distinct microbial populations can be targeted exclusively by using oligonucleotide probes or primers that target signature sequence information within the precursor 16S rRNA or mature 16S rRNA.

In a preferred embodiment, the method of the invention (also referred to herein as FISH-RiboSyn) is an in situ method that utilizes fluorescence in situ hybridization (FISH) with probes that target: (1) the 5' or 3' end of precursor 16S rRNA; or (2) the interior region of both precursor 16S rRNA and mature 16S rRNA. Images can be captured for a defined exposure time and the average fluorescent intensity for individual cells can be determined. The rate of increase of the whole cell fluorescent intensity is used to determine the specific rate of ribosome synthesis (or ribosome doubling time). The FISH-RiboSyn method can be attractive for rapidly measuring the specific growth rate (or cell doubling time) of distinct microbial populations within a mixed culture.

Another aspect of the invention is a kit for use in practicing the above method. The kit, in compartmental form, comprising a compartment adapted to contain one or more oligonucleotide probes or primers that target signature sequence information within the precursor 16S rRNA or mature 16S rRNA. Preferably, the primers are capable of participating in an amplification reaction of DNA comprising: (1) the 5' or 3' end of precursor 16S rRNA; or (2) the interior region of both precursor 16S rRNA and mature 16S rRNA. Preferably, the oligonucleotide probe targets (is capable of detecting): (1) the 5' or 3' end of precursor 16S rRNA; or (2) the interior region of both precursor 16S rRNA and mature 16S rRNA. Optionally, the kit contains another compartment adapted to contain reagents to conduct an amplification reaction. In one embodiment, the probe is labeled at its 5' end by a fluorogenic reporter molecule and at its 3' end by a molecule capable of quenching said fluorogenic molecule. In a specific embodiment, the probe is a fluorescently-labeled oligonucleotide hybridization probe targeting the precursor 16S rRNA for members of a selected genus, conjugated with a dye such as a cyanine dye.

The present invention is applicable to a range of industries including the medical, agricultural and industrial industries, including environmental protection, bioremediation, medical diagnosis, water quality control, or food quality control.

BRIEF DESCRIPTION OF THE DRAWINGS

The patent or application file contains at least one drawings executed in color. Copies of this patent or patent application publication with color drawing(s) will be provided by the Office upon request and payment of the necessary fee.

FIG. 10A; FISH: FIG. 10D), 10 minutes (DAPI: FIG. 10B; FISH: FIG. 10E), and 20 minutes (DAPI: FIG. 10C; FISH: FIG. 10F).

BRIEF DESCRIPTION OF THE SEQUENCES

Figure 1:
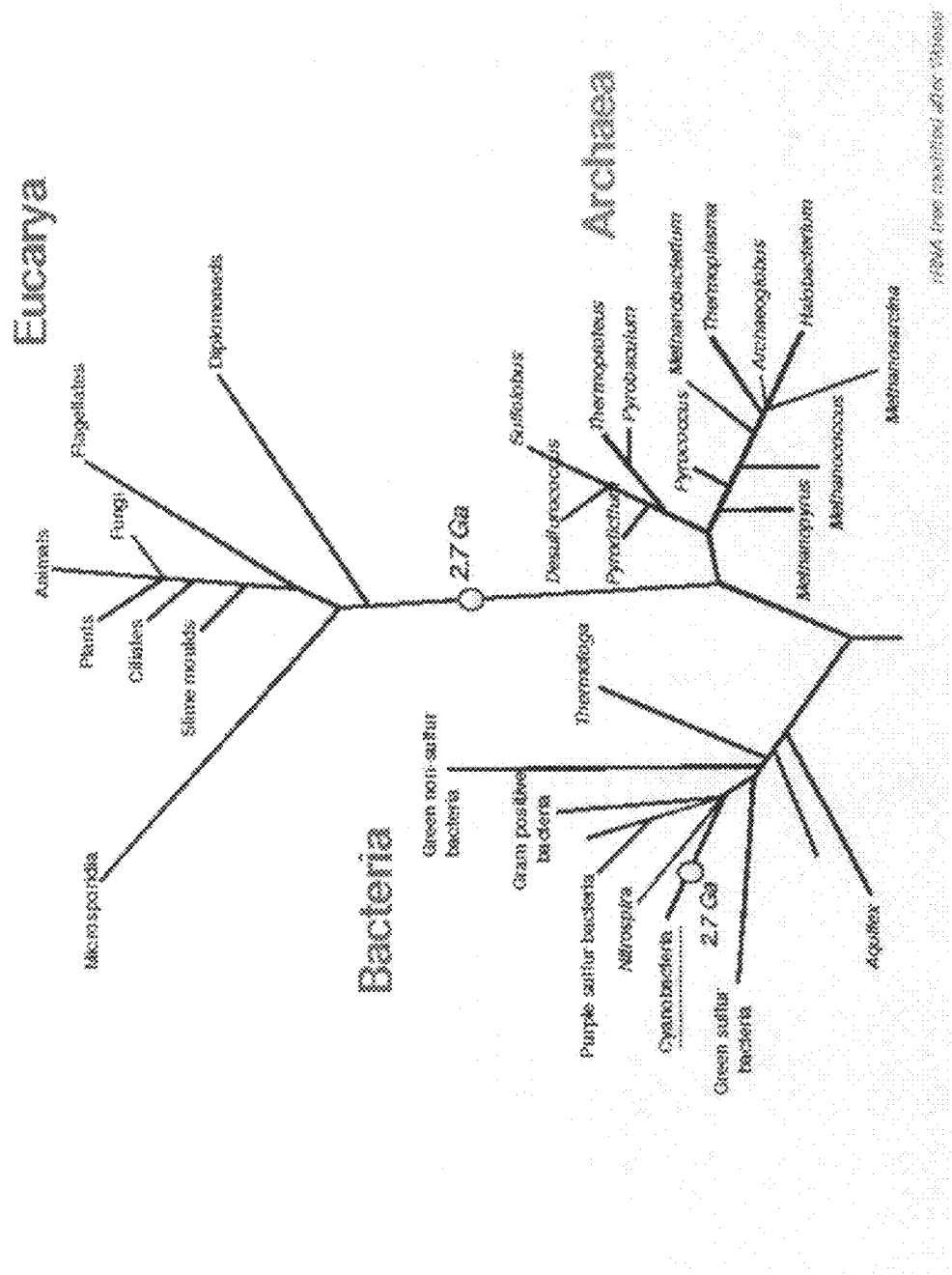
FIG. 1 shows a tree of life based on the comparison of 16S and 18S rRNA sequence from all life (from geobiology@mit). The canonical tree of life shows the evolutionary relationship of life on Earth. This tree was generated by computing the difference in sequence similarity of the 16S (or 18S for Eucarya) rRNA molecule, which is found in all life forms. The words at the end of the branches are the names for major groups of organisms. This is a very simple form of the tree; there are more detailed trees that include all of the genera. This tree provides the underlying framework for the methods of the invention, including the FISH (and FISH-RiboSyn) method. Each genus has a unique 16S (or 18S) rRNA molecule that can be targeted.
Figure 2:
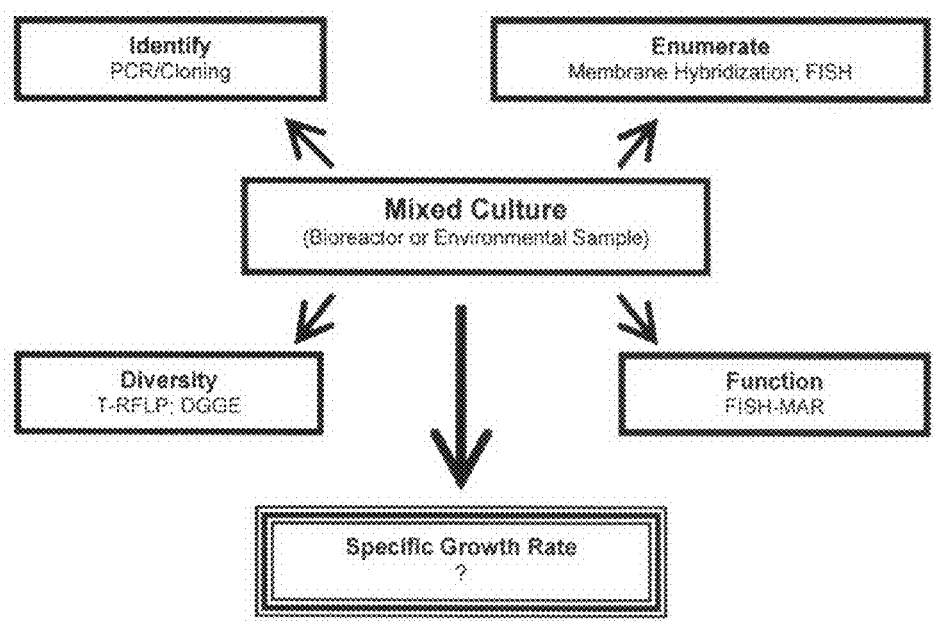
FIG. 2 shows molecular biology-based methods for investigation of specific microbial populations within a mixed culture. The types of information investigated are in bold. The molecular biology-based methods are listed below.
Figures 3A, 3B:
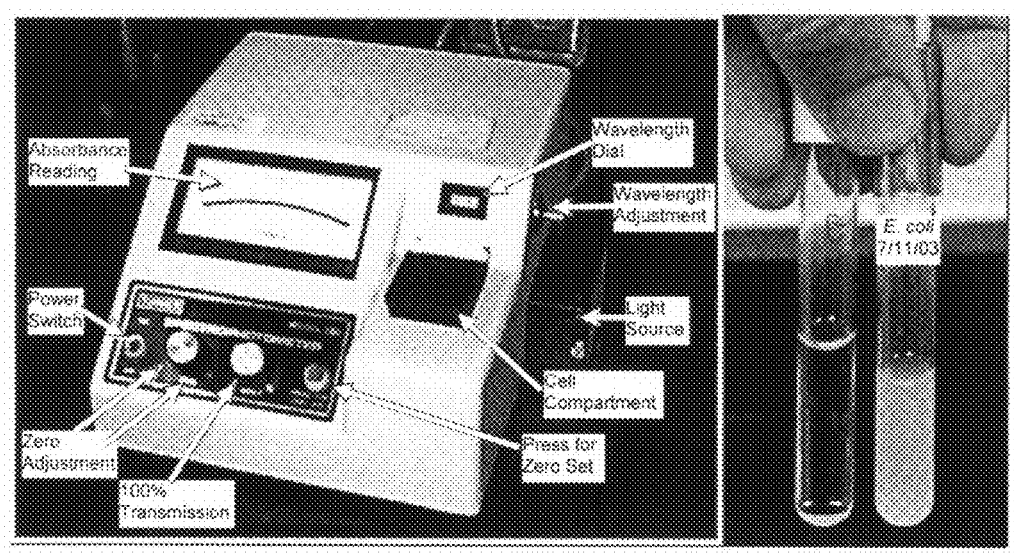
FIGS. 3A and 3B show a spectrophotometer (FIG. 3A) (from boomer web page) and tubes (FIG. 3B) that are the blank and the actively growing culture of $E.$ $coli$, representing the conventional method for measuring the specific growth rate of a pure culture.
Figure 4:
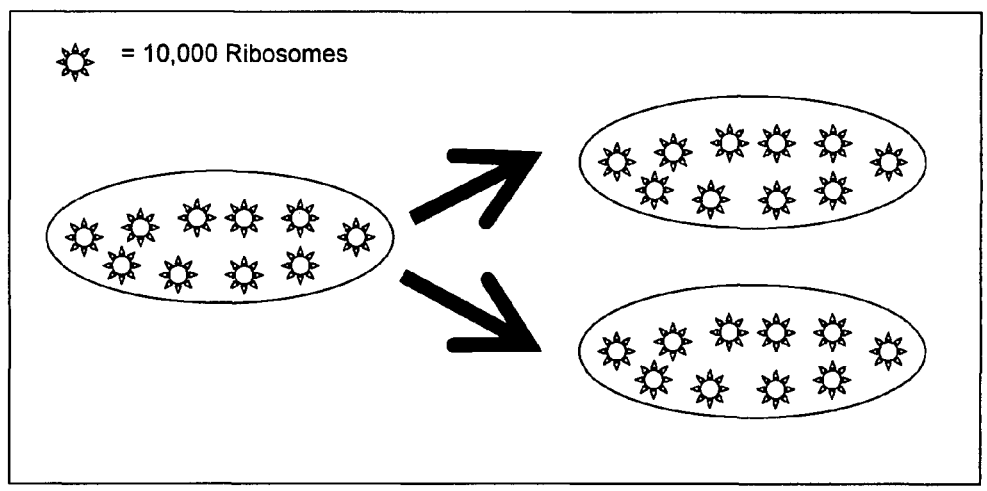
FIG. 4 shows doubling of cells and ribosomes during normal log growth.
Figure 5:
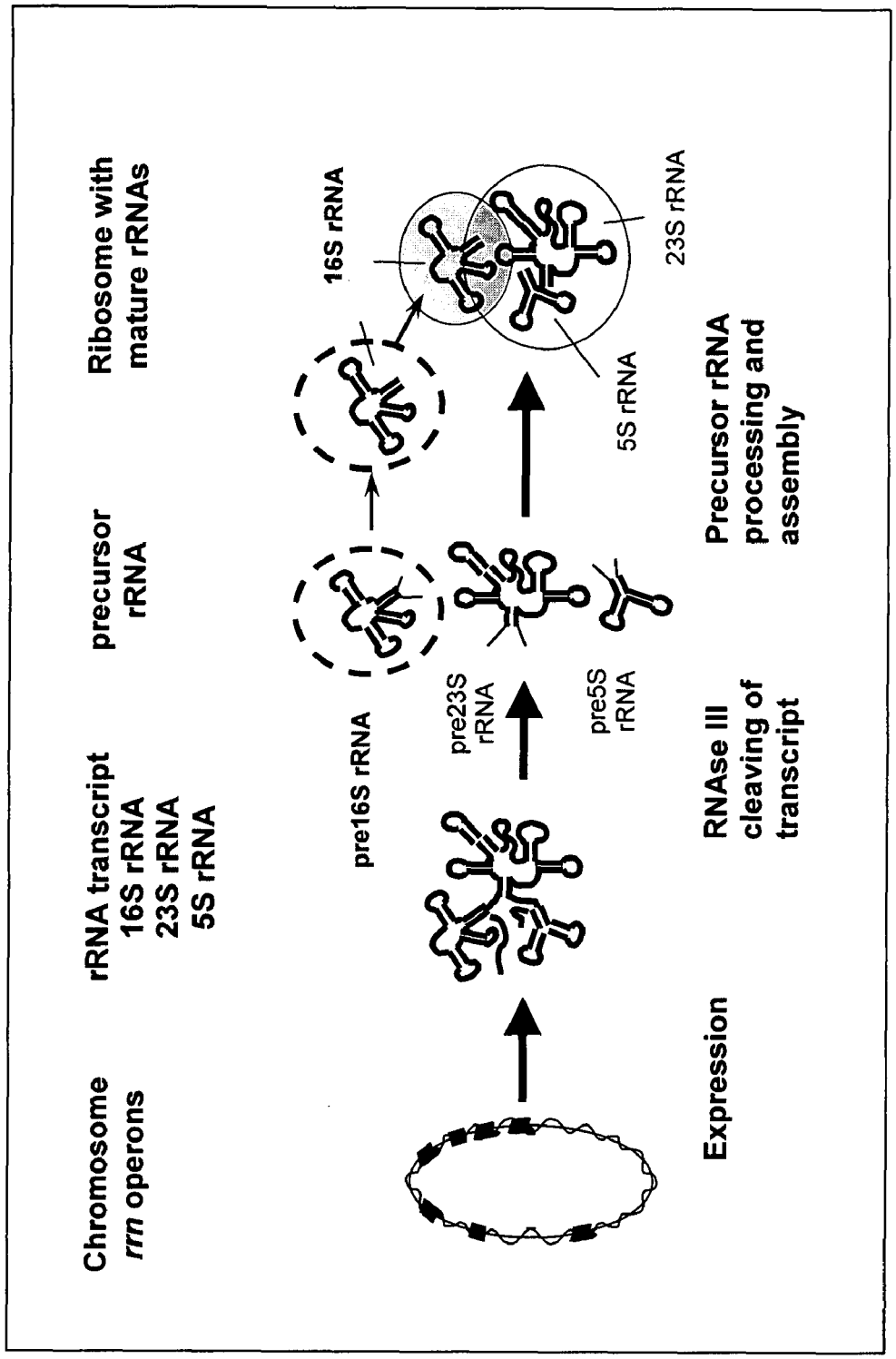
FIG. 5 shows normal ribosome synthesis for bacteria.
Figure 6:
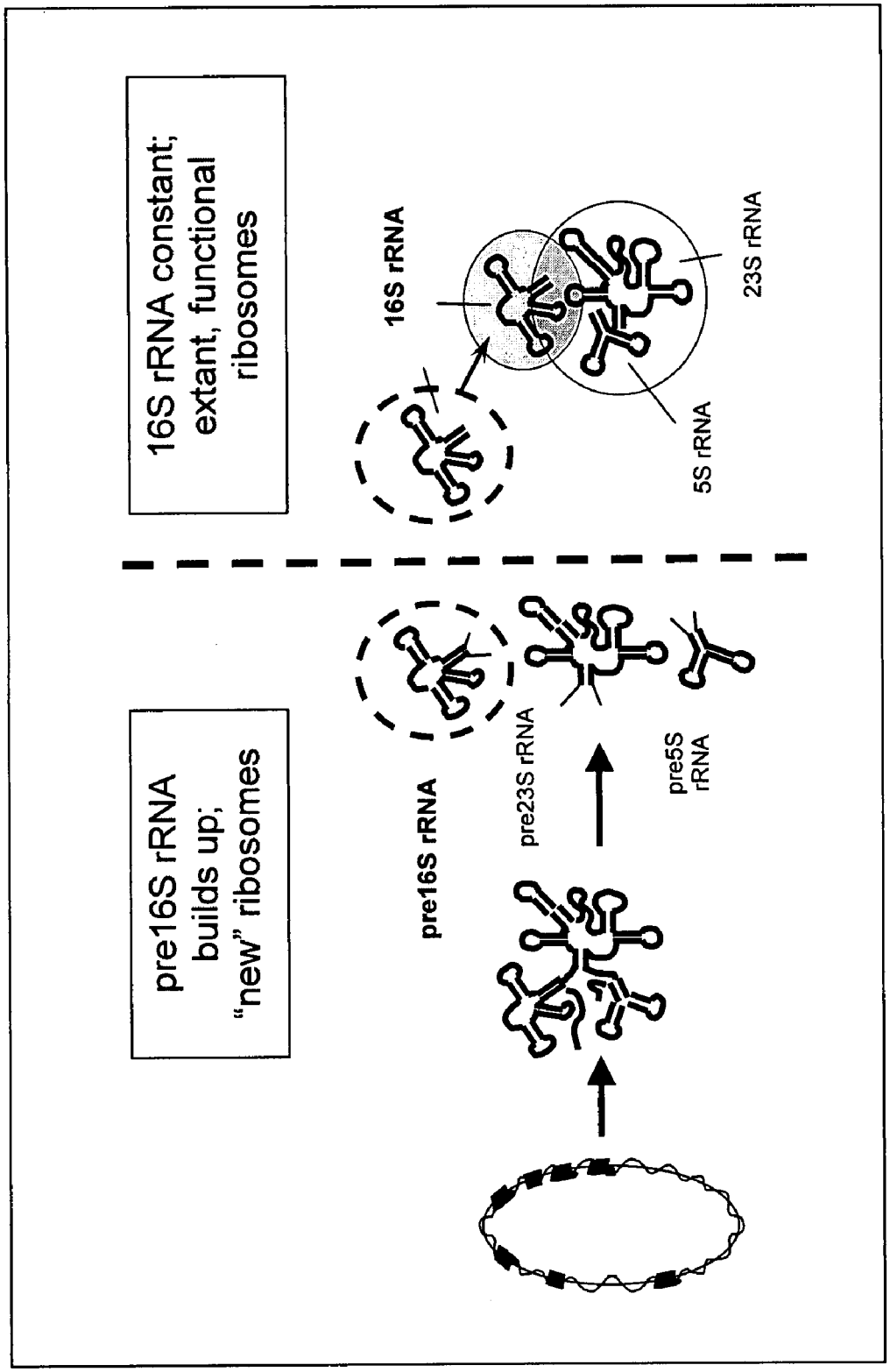
FIG. 6 shows that chloramphenicol inhibits ribosome synthesis leading to a buildup of pre16S rRNA.
Figure 7:
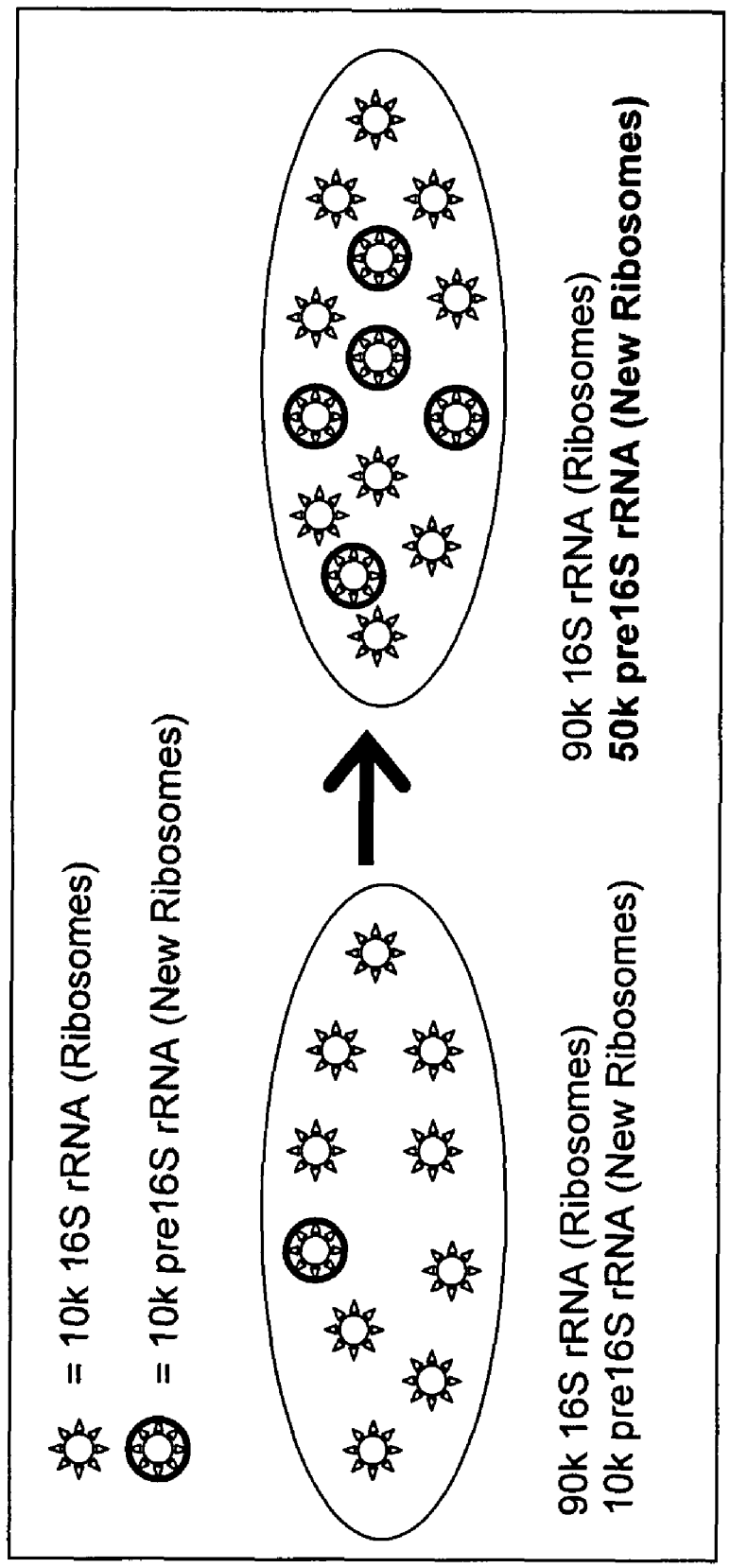
FIG. 7 shows the impact of chloramphenicol on pre16S and 16S rRNA levels in a cell during log growth.
Figures 8A, 8B, 8C, 8D:
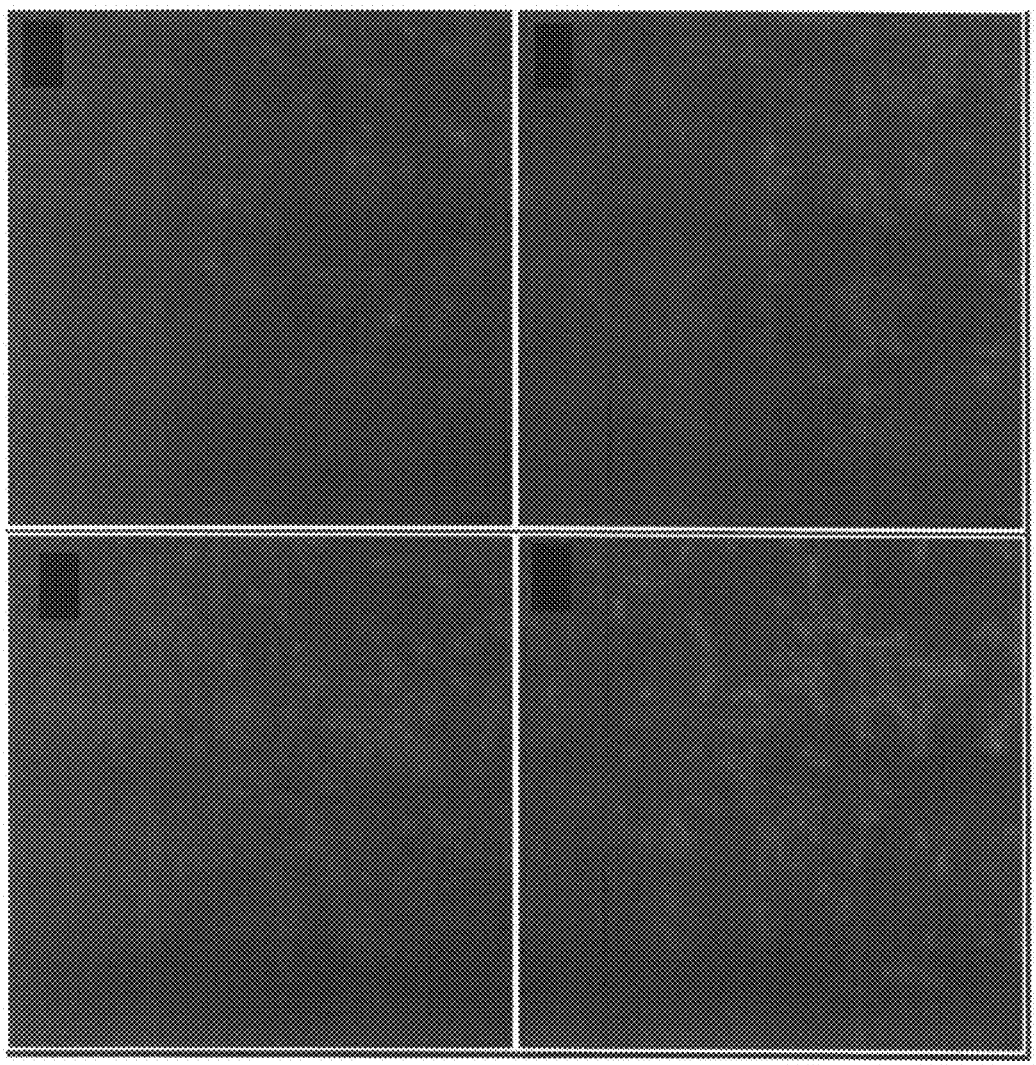
FIGS. 8A-8H represent preliminary data, showing FISH images (1000×) of a log phase culture of $A.$ $calcoaceticus$ exposed to chloramphenicol for 0 minutes (FIG. 8A), 3 minutes (FIG. 8B), 6 minutes (FIG. 8C), 9 minutes (FIG. 8D), 12 minutes (FIG. 8E), 15 minutes (FIG. 8F), 18 minutes (FIG. 8G), and 21 minutes (FIG. 8H).
Figures 8E, 8F, 8G, 8H:
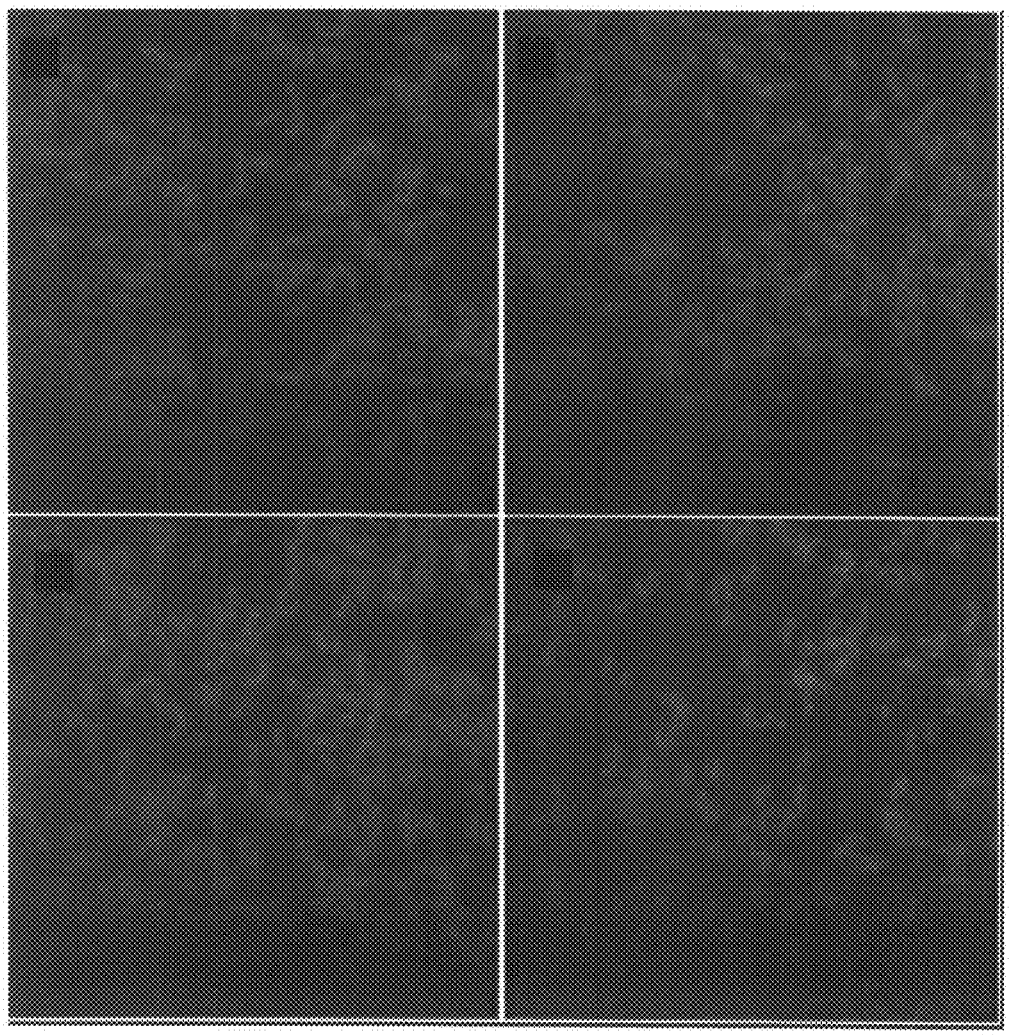
Figure 9:
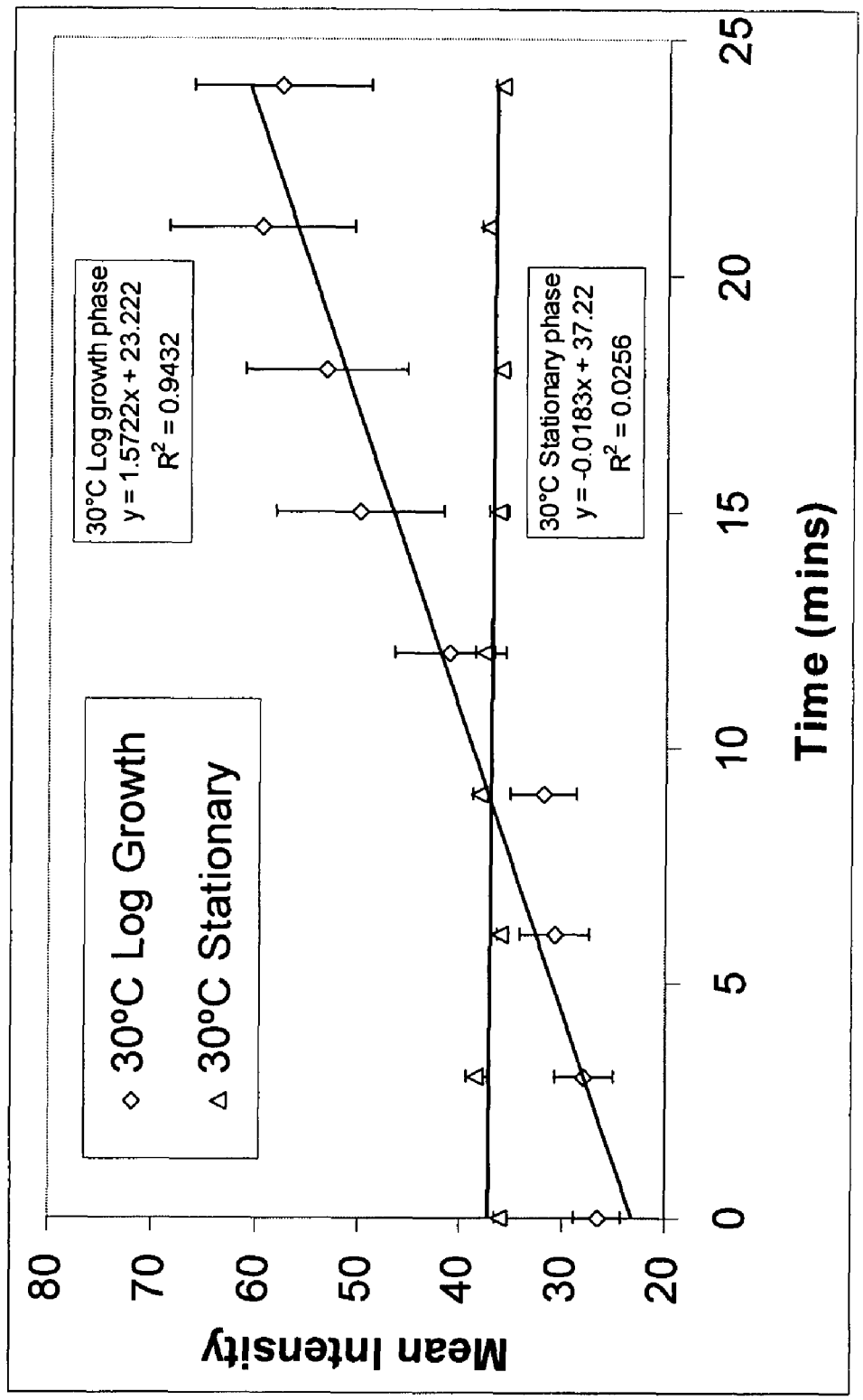
FIG. 9 represents preliminary data, showing mean intensity over time for two series of FISH images (1000×) corresponding to a log growth phase and stationary phase $A.$ $calcoaceticus$ culture exposed to chloramphenicol at various times.

SEQ ID NO:1 is the sequence of an oligonucleotide probe targeting the 16S rRNA of members of the genus $Nitrospira$ (Schramm, A. et al. $Appl.$ $Environ.$ $Microbiol.,$ 1998, 64:3480-3485).

SEQ ID NO:2 is the sequence of an oligonucleotide probe targeting the precursor 16S rRNA of members of the genus $Acinetobacter$ (Oerther, D. B. et al. $App$ $Environ$ $Microbiol,$ 2000, 66(5):2154-2165).

DETAILED DESCRIPTION OF THE INVENTION

The method of the invention can measure specific growth rate (cell doubling time) of a distinct microbial population within a non-homogeneous system (a mixed culture), such as samples from a biological reactor system or the environment.

In preferred embodiments, the method of the invention comprises:
 1) exposing a non-homogeneous system, such as a mixed culture sample, to chloramphenicol, or other protein synthesis inhibitor, in the existing environmental conditions;
 2) collecting samples over time (preferably, at defined times) from the non-homogeneous system that is exposed to the protein synthesis inhibitor; and
 3) analyzing the collected samples by a molecular biology-based method that will measure the rate of pre16S rRNA buildup (preferably, the rate of pre16S rRNA buildup can be measured in situ with FISH).

The specific growth rate (or cell doubling time) for a distinct microbial population can be determined and, optionally, monitored by its rate of pre16S rRNA buildup. Distinct microbial populations can be targeted exclusively by using oligonucleotide probes or primers that target signature sequence information within the precursor 16S rRNA or mature 16S rRNA.

The method of the invention measures the increase of pre16S rRNA in individual cells of a specific microbial population. FISH-RiboSyn is an in situ method that utilizes fluorescence in situ hybridization (FISH) with specific probes or primers that target: (1) 5' or 3' end of pre16S rRNA or (2) the interior region of both pre16S rRNA and mature 16S rRNA. Images are captured at defined exposure times and the average fluorescent intensity for individual cells can be determined. These intensities are used to calculate the rate of increase of the pre16S rRNA. When a sample is exposed to chloramphenicol or other protein synthesis inhibitor for defined times, the rate of increase of the pre16S is determined and the specific growth rate is calculated.

Optionally, in the various embodiments of the invention, the method further comprises recording the determined specific growth rate or specific rate of ribosome synthesis of a rapidly growing cell population in physical or electronic media. Preferably, the specific rate of ribosome synthesis and/or the specific growth rate are recorded or otherwise stored as units of synthesis or growth per unit of time. Optionally, the recorded growth or synthesis rate includes an annotation conveying the growth conditions (e.g., culture conditions) under which the determination was made, such as temperature. In one embodiment, the rate of pre16S rRNA buildup relative to the 16S rRNA is measured and input into a computer algorithm that then calculates the specific rate of ribosome synthesis. Optionally, the specific growth rate or the specific rate of ribosome synthesis can be displayed on an output device, such as an analog recorder, teletype machine, typewriter, facsimile recorder, cathode ray tube display, computer monitor, or other computation device. Optionally, the displayed specific growth rate or specific ribosome synthesis rate includes an annotation conveying the growth conditions (e.g., culture conditions) under which the determination was made (such as temperature).

Optionally, in the various embodiments of the invention, the method further comprises carrying out a manipulation of the non-homogeneous system based on the determined specific growth rate or specific ribosome synthesis rate. The manipulation can comprise, for example, a modification of culture conditions or the provision of a signal to induce expression of a polynucleotide of interest by one or more microbial populations within the system. In one embodiment, the manipulation comprises the addition of a substance that alters the metabolic rate of the one or more populations of microbes within the system. For example, the manipulation may comprise the addition of supplements such as carbon, nitrogen, and/or inorganic phosphates, or modification of temperature and/or pH.

Optionally, in the various embodiments of the invention, the method further comprises comparing the specific growth rate of a cell population within the non-homogeneous system, as determined above, to pre-existing growth rate data characterizing cell populations, such as microbial organisms. The pre-existing growth rate data of a cell population may be that specific growth rate observed under particular growth conditions (e.g., culture conditions), such as at a given temperature or at a given cell number or cell density, for example.

Optionally, in the various embodiments of the invention, the method further comprises introducing a test agent to the non-homogeneous system, or a sample thereof, before, during, or after introduction of the protein synthesis inhibitor, in order to determine whether the test agent exerts a biological effect on the microbes. The test agent may be a member of a combinatorial library, for example. In one embodiment, the method includes contacting the non-homogeneous system, or a sample thereof, with one or more members of a library of agents for the purpose of monitoring the effect on specific growth rate. Optionally, the method further comprises comparing the specific growth rate of a particular microbial population within the non-homogeneous system before and after introduction of the test agent. The particular microbial population may be one that is determined to be rapidly growing in the presence or absence of the test agent, for example.

In the method and kit of the invention, the probe and primer is preferably genus-specific, species-specific, or strain-specific. Reference herein to "primer" or "probe" is not to be taken as any limitation as to structure, size, or function. The primer may be used as an amplification molecule or may be used as a probe for hybridization purposes.

Another aspect of the invention is a kit for use in practicing the above method. The kit, in compartmental form, comprising a compartment adapted to contain one or more oligonucleotide probes or primers that target signature sequence information within the precursor 16S rRNA or mature 16S rRNA. Preferably, the primers are capable of participating in an amplification reaction of DNA comprising: (1) the 5' or 3' end of precursor 16S rRNA; or (2) the interior region of both precursor 16S rRNA and mature 16S rRNA. Preferably, the oligonucleotide probe targets: (1) the 5' or 3' end of precursor 16S rRNA; or (2) the interior region of both precursor 16S rRNA and mature 16S rRNA. Optionally, the kit contains another compartment adapted to contain reagents to conduct an amplification reaction. In one embodiment, the probe is labeled at its 5' end by a fluorogenic reporter molecule and at its 3' end by a molecule capable of quenching said fluorogenic molecule. In a specific embodiment, the probe is a fluorescently-labeled oligonucleotide hybridization probe targeting the precursor 16S rRNA for members of a selected genus, conjugated with a dye such as a cyanine dye.

As indicated above, kits of the invention include reagents for use in the methods described herein, in one or more containers. The kits may include primers and/or probes, buffers, and/or excipients, separately or in combination. Each reagent can be supplied in a solid form or liquid buffer that is suitable for inventory storage. Kits may also include means for obtaining a biological sample of a tissue or biological fluid from a host organism or an environmental sample.

Kits of the invention are provided in suitable packaging. As used herein, "packaging" refers to a solid matrix or material customarily used in a system and capable of holding within fixed limits one or more of the reagent components for use in a method of the present invention. Such materials include glass and plastic (e.g., polyethylene, polypropylene, and polycarbonate) bottles, vials, paper, plastic, and plastic-foil laminated envelopes and the like. Preferably, the solid matrix is a structure having a surface that can be derivatized to anchor an oligonucleotide probe or primer. Preferably, the solid matrix is a planar material such as the side of a microtitre well or the side of a dipstick. In one embodiment, the kit includes a microtitre tray with two or more wells and with reagents including primers or probes in the wells.

The one or more probes or primers in the kit may be immobilized to the compartments. Methods for linking nucleic acid molecules to solid supports are well known in the art. Processes for linking the primer or probe to the solid matrix include amide linkage, amidate linkage, thioether linkage, and the introduction of amino groups on to the solid matrix. The kit may be conveniently adapted for automated or semi-automated use. The kit may include a plurality of primers and/or probes that target either the 5' or 3' end of pre16S rRNA, or the interior region of both pre16S rRNA and mature 16S rRNA, to permit the detection and determination of specific growth rate of more than one microbe. Optionally, the probes and primers are arrayed in the compartments of the kits.

Kits of the invention may optionally include a set of instructions in printed or electronic (e.g., magnetic or optical disk) form, relating information regarding the components of the kits and/or how to measure specific growth rate of a microbe. The kit may also be commercialized as part of a larger package that includes instrumentation for measuring other biochemical components, such as, for example, a mass spectrometer.

The method and kit of the invention will be useful to scientists and engineers that share an interest in determining how fast microbes are growing. Industries that may benefit include, but are not limited to, environmental systems (water and wastewater treatment systems), bioremediation (optimization of conditions for microbial growth), public health (identification of rapidly growing infectious microbes), and homeland security (identification of rapidly growing bioterrorism agents).

The method and kit of the invention can be useful to the environmental engineering and science disciplines (academic, private, and public sectors), as well as for clinical diagnosis of infectious agents. Current methods for diagnosis include culture-based methods and the use of some molecular biology-based methods that typically identify and enumerate. The present inventors offer the only method for measuring the specific growth rate for an infectious agent. For an infection involving multiple bacteria types, the method of the invention can be used to identify the rapidly growing pathogen. If this method is adopted by hospitals, the number of samples analyzed could increase dramatically.

After the terrible events of Sep. 11, 2001 and the anthrax attacks, the number of clinical and environmental samples that were screened increased to 125,000 and 1 million, respectively. The method and kit of the invention may be useful in screening samples for actively growing bioterrorism (BT) agents.

The mixed culture sample may be a biological sample. One or more biological samples can be obtained from an individual. The biological sample may be obtained by any method known in the art. Samples may be collected at a single time point or at multiple time points from one or more tissues or bodily fluids. The tissue or fluid may be collected using standard techniques in the art, such as, for example, tissue biopsy, blood draw, or collection of secretia or excretion from the body. Examples of suitable bodily fluids or tissues from which an infectious agent, or component thereof, may be isolated include urine, blood, intestinal fluid, edema fluid, saliva, lacrimal fluid (tears), inflammatory exudate, synovial fluid, abscess, empyema or other infected fluid, cerebrospinal fluid, pleural effusions, sweat, pulmonary secretions, seminal fluid, feces, bile, intestinal secretions, or any infected tissue including, but not limited to liver, intestinal epithelium, spleen, lung, pericardium, pleura, skin, muscle, synovium, cartilage, bone, bone marrow, thyroid gland, pancreas, brain, prostate, ovaries, endometrium, uterus, uterine cervix, testes, epididymis, bladder wall, kidney, adrenal, pituitary gland, adipose cells/tissue, omentum, or other cells and tissue. The frequency of obtaining one or more biological samples can vary.

The various methods employed in the preparation of plasmids and transformation of host organisms are well known in the art and are described, for example, in U.S. Pat. Nos. 5,011,909 and 5,130,253. These patents are incorporated herein by reference in their entirety. These procedures are also described in Maniatis, et al. (1982) *Molecular Cloning: A Laboratory Manual*, Cold Spring Harbor Laboratory, New York. Thus, it is within the skill of those in the genetic engineering art to extract DNA from its source, perform restrictions enzyme digestions, electrophorese DNA fragments, tail and anneal plasmid and insert DNA, ligate DNA, transform cells, e.g., *E. coli* or plant cells, prepare plasmid DNA, electrophorese proteins, and sequence DNA.

The cells assayed for specific growth rate in accordance with the method of the invention may be genetically modified (e.g., recombinant) or non-genetically modified. If a vector is used to genetically modify the cell, it may be in the form of a plasmid, a viral particle, a phage, etc. Transformed (genetically modified) cells can be cultured in conventional nutrient media modified as appropriate for activating promoters, selecting transformants/transfectants or amplifying the subunit-encoding polynucleotide. The culture conditions, such as temperature, pH and the like, generally are similar to those previously used with the host cell selected for expression, and will be apparent to those of skill in the art.

Primers capable of participating in an amplification reaction of the template nucleic acids comprising precursor 16S rRNA (e.g., amplification of the 5' or 3' end of precursor 16S rRNA; or the interior region of both precursor 16S rRNA and mature 16S rRNA) and 16S rRNA-specific oligonucleotide probes targeting (capable of detecting) the precursor 16S rRNA (e.g., targeting the 5' or 3' end of precursor 16S rRNA; or the interior region of both precursor 16S rRNA and mature 16S rRNA) can be utilized in the invention, as described above.

Oligonucleotides can be of any suitable size, which depends on many factors, including the function or use of the oligonucleotide. Oligonucleotides can be prepared by any suitable method, including, for example, cloning, enzymatic restriction of larger nucleotides, and direct chemical synthesis by a method such as the phosphotriester method of Narang et al., *Meth. Enzymol.* 68:90-9 (1979), the phosphodiester method of Brown et al., *Meth. Enzymol.* 68:109-51 (1979), the diethylphosphoramidite method of Beaucage et al., *Tetrahedron Lett.* 22:1859-62 (1981), and the solid support method of U.S. Pat. No. 4,458,066. A review of synthesis methods is provided in Goodchild, *Bioconjugate Chemistry* 1:165-87(1990).

The term "primer" refers to an oligonucleotide, whether natural or synthetic, capable of acting as an initiating point for DNA synthesis under conditions in which synthesis of a primer extension product complementary to a nucleic acid strand is induced. For example, such conditions include inclusion of four different nucleoside triphosphates and an agent for polymerization (i.e., DNA polymerase or reverse transcriptase) in an appropriate buffer and at a suitable temperature. A primer can be a single-stranded oligodeoxyribonucleotide. The length of a primer can vary and depends on the intended use of the primer. In one embodiment, a primer is less than 40 nucleotides. In another embodiment, a primer ranges from 15 to 35 nucleotides.

A primer need not reflect the exact sequence of the template, but should be sufficiently complementary to hybridize with a template. Primers can incorporate additional features which allow for the detection or immobilization of the primer, but do not alter the basic ability of the primer to act as a point of initiation of DNA synthesis.

The primers and oligonucleotide probes may be manufactured using any convenient method of synthesis. Examples of such methods may be found in standard textbooks, for example "Protocols for Oligonucleotides and Analogues; Synthesis and Properties," Methods in Molecular Biology Series; Volume 20; Ed. Sudhir Agrawal, Humana ISBN:

0-89603-247-7; 1993; 1st Edition. The primers and probes can be produced by recombinant or synthetic techniques. If desired, the primer(s) may be labeled to facilitate detection.

The isolated polynucleotides (e.g., oligonucleotide detection probes and primers) used in the invention are capable of selectively hybridizing to a nucleic acid sequence of the precursor 16S rRNA (e.g., amplification of the 5' or 3' end of precursor 16S rRNA; or the interior region of both precursor 16S rRNA and mature 16S rRNA). An oligonucleotide probe will typically comprise a contiguous/consecutive span of at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 or more nucleotides. In one embodiment, the oligonucleotide probe is 17-50 nucleotides. In another embodiment, the oligonucleotide probe is 17-30 nucleotides. In another embodiment, the oligonucleotide probe is 17-30 nucleotides.

The design of such probes and primers will be apparent to the molecular biologist of ordinary skill. Typically, the oligonucleotide probe (also referred to herein as the "detection probe", "sequence-specific probe", or "16S rRNA-specific probe") comprises a recognition sequence that is partially or fully complementary to a target nucleic acid sequence (e.g., DNA or RNA), in this case, a nucleic acid sequence of precursor 16S rRNA. Optionally, the recognition sequence is substituted with high-affinity nucleotide analogues to increase the sensitivity and/or specificity of conventional oligonucleotides, for hybridization to target sequences.

Such probes are of any convenient length such as up to 50 nucleotides, up to 40 nucleotides, and more conveniently up to 30 nucleotides in length, such as for example 8-25 or 8-15 nucleotides in length. In general, such probes will comprise base sequences entirely complementary to the corresponding locus of the target sequence. However, if required, one or more mismatches may be introduced, provided that the discriminatory power of the oligonucleotide probe is not unduly affected. The probes may carry one or more labels to facilitate detection.

The label of the labeled probes and primers can be any type of detectable substance, such as a radioactive label, enzyme label, chemiluminescent label, fluorescent label, or magnetic label. Alternatively, non-labeled nucleotide sequences may be used directly as probes or primers; however, the sequences are generally labeled with a radioactive element ($^{32}P$, $^{35}S$, $^{3}H$, $^{125}I$) or with a molecule such as biotin, acetylaminofluorene, digoxigenin, 5-bromo-deoxyuridine, or fluorescein to provide probes that can be used in numerous applications.

In some embodiments, the oligonucleotide probe comprises a fluorophore moiety and a quencher moiety, positioned in such a way that the hybridized state of the probe can be distinguished from the unhybridized state of the probe by an increase in the fluorescent signal from the nucleotide. In one aspect, the detection probe comprises, in addition to the recognition sequence (also known as the recognition element), first and second complementary sequences, which specifically hybridize to each other when the probe is not hybridized to a recognition sequence in a target molecule, bringing the quencher molecule in sufficient proximity to the reporter molecule to quench fluorescence of the reporter molecule. Hybridization of the target sequence distances the quencher from the reporter molecule and results in a signal, which is proportional to the amount of hybridization.

In this particular context, the term "label" means a reporter group, which is detectable either by itself or as a part of a detection series. Examples of functional parts of reporter groups are biotin, digoxigenin, fluorescent groups (groups which are able to absorb electromagnetic radiation, e.g., light or X-rays, of a certain wavelength, and which subsequently reemits the energy absorbed as radiation of longer wavelength; illustrative examples are DANSYL (5-dimethylamino)-1-naphthalenesulfonyl), DOXYL (N-oxyl-4,4-dimethyloxazolidine), PROXYL (N-oxyl-2,2,5,5-tetramethylpyrrolidine), TEMPO(N-oxyl-2,2,6,6-tetramethylpiperidine), dinitrophenyl, acridines, coumarins, Cy3 and Cy5 (trademarks for Biological Detection Systems, Inc.), erythrosine, coumaric acid, umbelliferone, Texas red, rhodamine, tetramethyl rhodamine, Rox, 7-nitrobenzo-2-oxa-1-diazole (NBD), pyrene, fluorescein, Europium, Ruthenium, Samarium, and other rare earth metals), radio isotopic labels, chemiluminescence labels (labels that are detectable via the emission of light during a chemical reaction), spin labels (a free radical (e.g., substituted organic nitroxides) or other paramagnetic probes (e.g., $Cu^{2+}$, $Mg^{2+}$) bound to a biological molecule being detectable by the use of electron spin resonance spectroscopy). Particular examples of such labels are biotin, fluorescein, Texas Red, rhodamine, dinitrophenyl, digoxigenin, Ruthenium, Europium, cyanine dyes such as Cy5 and Cy3, etc. In one embodiment, the label is a dye, such as a cyanine dye, conjugated to the oligonucleotide probe (e.g., Cy3).

Preferably, the probe or primer specifically hybridizes with at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides of the target sequence (such as the 5' or 3' end of precursor 16S rRNA; or the interior region of both precursor 16S rRNA and mature 16S rRNA). Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under low, intermediate, or high stringency conditions by techniques well known in the art, as described, for example, in Keller, G. H., M. M. Manak, 1987, *DNA Probes*, Stockton Press, New York, N.Y., pp. 169-170.

For example, hybridization of immobilized DNA on Southern blots with $^{32}P$-labeled gene-specific probes can be performed by standard methods (Maniatis et al. [1982] *Molecular Cloning: A Laboratory Manual*, Cold Spring Harbor Laboratory, New York). In general, hybridization and subsequent washes can be carried out under intermediate to high stringency conditions that allow for detection of target sequences with homology to the exemplified polynucleotide sequence. For double-stranded DNA gene probes, hybridization can be carried out overnight at 20-25° C. below the melting temperature ($T_m$) of the DNA hybrid in 6×SSPE, 5×Denhardt's solution, 0.1% SDS, 0.1 mg/ml denatured DNA. The melting temperature is described by the following formula (Beltz et al. [1983] *Methods of Enzymology*, R. Wu, L. Grossman and K. Moldave [eds.] Academic Press, New York 100:266-285).

$$Tm = 81.5°\,C. + 16.6\,\text{Log}\,[Na^+] + 0.41(\%\,G+C) - 0.61(\%\,\text{formamide}) - 600/\text{length of duplex in base pairs}.$$

Washes are typically carried out as follows:
(1) twice at room temperature for 15 minutes in 1×SSPE, 0.1% SDS (low stringency wash);
(2) once at $T_m - 20°$ C. for 15 minutes in 0.2×SSPE, 0.1% SDS (intermediate stringency wash).

For oligonucleotide probes, hybridization can be carried out overnight at 10-20° C. below the melting temperature ($T_m$) of the hybrid in 6×SSPE, 5×Denhardt's solution, 0.1% SDS, 0.1 mg/ml denatured DNA. $T_m$ for oligonucleotide probes can be determined by the following formula:

$T_m$(° C.)=2(number T/A base pairs)+4(number G/C base pairs) (Suggs et al. [1981] *ICN-UCLA Symp. Dev. Biol. Using Purified Genes*, D. D. Brown [ed.], Academic Press, New York, 23:683-693).

Washes can be carried out as follows:
(1) twice at room temperature for 15 minutes 1×SSPE, 0.1% SDS (low stringency wash);
2) once at the hybridization temperature for 15 minutes in 1×SSPE, 0.1% SDS (intermediate stringency wash).

In general, salt and/or temperature can be altered to change stringency. With a labeled DNA fragment >70 or so bases in length, the following conditions can be used:

| | |
|---|---|
| Low: | 1 or 2X SSPE, room temperature |
| Low: | 1 or 2X SSPE, 42° C. |
| Intermediate: | 0.2X or 1X SSPE, 65° C. |
| High: | 0.1X SSPE, 65° C. |

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in pre-hybridization mixture containing 100 µg/ml denatured salmon sperm DNA and 5-20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Another non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein the mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

A "complementary" polynucleotide sequence, as used herein, generally refers to a sequence arising from the hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. A "complementary" polynucleotide sequence may also be referred to as an "antisense" polynucleotide sequence or an "antisense sequence".

The term "label", as used herein, refers to any atom or molecule that can be used to provide a detectable (preferably, quantifiable) signal, and which can be attached to a nucleic acid or protein. Labels may provide signals detectable by fluorescence, radioactivity, calorimetric, X-ray diffraction or absorption, magnetism, enzymatic activity, and the like.

The terms "recombinant host cells", "host cells", "cells", "cell lines", "cell cultures", and other such terms refer to prokaryotic or eukaryotic cells which can be, or have been, used as recipients for recombinant vectors or other transfer DNA, immaterial of the method by which the DNA is introduced into the cell or the subsequent disposition of the cell. Thus, the cells subjected to the method of the invention can be, for example, any bacterial cells (e.g., Gram-positive, Gram-negative, those not lending themselves to Gram stain, aerobic, anaerobic, etc.), yeast cells, vertebrate cells (such as human or non-human mammalian cells), invertebrate cells, etc. The terms include the progeny of the original cell that has been transfected. The term "recombinant" when used with reference to a cell, or polynucleotide, polypeptide, or vector, indicates that the cell, polynucleotide, polypeptide or vector, has been modified by the introduction of a heterologous nucleic acid or amino acid or the alteration of a native nucleic acid or amino acid, or that the cell is derived from a cell so modified. A polypeptide of interest can be encoded by a gene that is part of the cell's genome, but for which regulatory sequences have been modified to provide increased levels of expression. Thus, recombinant cells can express genes that are not found within the native (non-recombinant) form of the cell or express native genes that are otherwise abnormally expressed, under expressed or not expressed at all. The prokaryotic or eukaryotic cells subjected to the method of the invention may be recombinant cells, un-modified cells, or a mixture thereof.

The term "genetic modification" as used herein refers to the stable or transient alteration of the genotype of a cell by intentional introduction of exogenous nucleic acids by any means known in the art (including for example, direct transmission of a polynucleotide sequence from a cell or virus particle, transmission of infective virus particles, and transmission by any known polynucleotide-bearing substance) resulting in a permanent or temporary alteration of genotype. The nucleic acids may be synthetic, or naturally derived, and may contain genes, portions of genes, or other useful polynucleotides. A translation initiation codon can be inserted as necessary, making methionine the first amino acid in the sequence. The terms "transfection" and "transformation" are used interchangeably herein to refer to the insertion of an exogenous polynucleotide into a host cell, irrespective of the method used for the insertion, the molecular form of the polynucleotide that is inserted, or the nature of the cell (e.g., prokaryotic or eukaryotic). The insertion of a polynucleotide per se and the insertion of a plasmid or vector comprised of the exogenous polynucleotide are included. The exogenous polynucleotide may be directly transcribed and translated by the cell, maintained as a nonintegrated vector, for example, a plasmid, or alternatively, may be stably integrated into the host genome.

Examples of microorganisms that may be assayed for cell growth rate in accordance with the method of the invention include, but are not limited, to those of importance to wastewater and waste treatment processes (e.g., nitrifying bacteria, phosphorus accumulating organisms, and methanogens), public health (e.g., coliforms and bioterrorism agents) and food safety (e.g., botulism). Examples of potential bacterial cells of interest include, but are not limited to, *Nitrospira* spp., *Nitrosospira* spp., *Nitrobacter* spp., *Nitrosomonas* spp., *Clostridium* spp., *Bacillus* spp. (such as *Bacillus anthracis*), methogenic archaea, coliforms (such as *E. coli*), *Salmonella* spp., and *Bacteroides* spp.

The medium used to cultivate the cells may be any conventional medium suitable for growing the populations of cells in question and, optionally, obtaining expression of a gene of interest. Cells can be grown under amenable culture conditions, i.e., appropriate conditions of temperature, pH, humidity, oxygen, and nutrient availability including carbon/energy sources. Suitable media are available from commercial suppliers or may be prepared according to published protocols (e.g., as described in catalogues of the American Type Culture Collection).

Gene products secreted from the cell populations in the mixed culture or samples derived there from may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

The exposing (e.g., contacting) steps of the method of the invention can involve combining or mixing the non-homogeneous sample and the protein synthesis inhibitor, or the probe or primers, in a suitable receptacle, such as a reaction vessel, microvessel, tube, microtube, well, or other solid support. Samples, protein synthesis inhibitors, and/or probes or primers may be arrayed on a solid support, such as a multi-well plate. Likewise, the sampling and analyzing (determining) steps can take place in an arrayed format on a solid support, such as a multi-well plate. "Arraying" refers to the act of organizing or arranging members of a library (e.g., an array of different samples, an array of protein synthesis inhibitors, or an array of primers or probes that target signature sequence information within the precursor 16S rRNA or mature 16S rRNA), or other collection, into a logical or physical array. Thus, an "array" refers to a physical or logical arrangement of, e.g., library members (e.g., mixed culture library members). A physical array can be any spatial format or physically gridded format in which physical manifestations of corresponding library members are arranged in an ordered manner, lending itself to combinatorial screening. For example, samples corresponding to individual or pooled members of a sample library can be arranged in a series of numbered rows and columns, e.g., on a multiwell plate. Similarly, sensors can be plated or otherwise deposited in microtitered, e.g., 96-well, 384-well, or -1536 well, plates (or trays). Optionally, the protein synthesis inhibitors, primers, and probes may be immobilized on the solid support with retention of function. Methods for linking nucleic acid molecules and proteins to solid supports are well known in the art. Processes for linking the primer or probe to the solid matrix include amide linkage, amidate linkage, thioether linkage, and the introduction of amino groups on to the solid matrix.

As used herein, the term "protein synthesis inhibitor" is intended to refer to bacteriostatic agents that inhibit the secondary processing of precursor 16S rRNA, but do not inhibit the production of precursor 16S rRNA. For example, chloramphenicol, lincomycin, and erythromycin, are ribosomally active antibiotics that block the formation of peptide bonds by binding at or near the aminoacyl tRNA binding site on the large ribosomal subunit. After some time, the previously synthesized peptidyl tRNA is released and hydrolyzed. The ribosomal subunits are then released from the mRNA and are free to rejoin other mRNA molecules to start another abortive cycle. This leads to a truncated version of the ribosome cycle. Thus, these drugs inhibit protein synthesis at the chain elongation step, leading to premature association of the active complex. As a result, when these antibiotics are withdrawn, many free ribosomes are present and ready to resume normal protein synthesis. This explains why the action of these drugs is reversible and why these antibiotics are bacteriostatic instead of bacteriocidal. The protein synthesis inhibitor may be one that inhibits the secondary processing of rRNA in prokaryotic cells, eukaryotic cells, or both cell types.

As used herein, the terms "non-homogeneous system", "non-homogeneous sample", "mixed system", and "mixed sample" are interchangeable and refer to a mixture of two or more cell populations (such as microbial populations), e.g., a mixed culture sample. The non-homogeneous system or sample can be any composition of matter of interest, in any physical state (e.g., solid, liquid, semi-solid, vapor) and of any complexity, such as a biological sample (e.g., a bodily fluid, plant or seed material) or environmental sample (e.g., water, soil, slurry). Preferably, the sample is a fluid, such as a bodily fluid. The sample may be contained within a test tube, culture vessel, fermentation tank, multi-well plate, or any other container or supporting substrate. The sample can be, for example, a cell culture, human or animal tissue (such as flesh, blood, saliva, semen, vaginal secretion, urine, tears, perspiration, extracellular fluid, etc.), or an environmental sample, such as water, soil, or sludge. The sample can be a small-scale or large scale fermentation.

The "complexity" of a sample refers to the number of different microbial species that are present in the sample.

The terms "body fluid" and "bodily fluid", as used herein, refer to a mixture of molecules obtained from a patient. Bodily fluids include, but are not limited to, exhaled breath, whole blood, blood plasma, urine, semen, saliva, lymph fluid, meningal fluid, amniotic fluid, glandular fluid, sputum, feces, sweat, mucous, and cerebrospinal fluid. Bodily fluid also includes experimentally separated fractions of all of the preceding solutions or mixtures containing homogenized solid material, such as feces, tissues, and biopsy samples.

Biological samples (samples of biological origin) includes those that are accessible from an organism through sampling by invasive means (e.g., surgery, open biopsy, endoscopic biopsy, and other procedures involving non-negligible risk) or by minimally invasive or non-invasive approaches (e.g., urine collection, blood drawing, needle aspiration, and other procedures involving minimal risk, discomfort or effort). The definition also includes samples that have been manipulated in any way after their procurement, such as by treatment with reagents, solubilization, or enrichment for certain components, such as proteins, organic metabolites, or microbes. The term "biological sample" also encompasses a clinical sample such as serum, plasma, other biological fluid, or tissue samples, and also includes cells in culture, cell supernatants and cell lysates.

As used herein, the terms "population" and "cell population" are intended to refer to a distinguishable group of eukaryotic or prokaryotic cells, such as a genus, species or strain of microorganism. A population can differ from other populations by phylogenetic profile or by some other detectable genotype and/or phenotype. Using the method of the invention, populations can be distinguished from each other based on specific growth rate and length heterogeneity of the pre16S RT&PE products. A population can comprise two or more sub-populations that differ from each other by some detectable genotype and/or phenotype. A non-homogeneous system such as a mixed culture can be so small as to comprise two populations or can be larger, e.g., $10^{12}$ populations. In some embodiments, a mixed culture is between five and 20 different populations, as well as up to hundreds or thousands of different populations. Those skilled in the art can readily determine a suitable size and diversity of a population sufficient for a particular application.

The terms "microbe" and "microbial cell" are inclusive of all prokaryotic microorganisms with a protein synthesis pathway susceptible to suppression by the protein synthesis inhibitor utilized in accordance with the invention. The microbe may be pathogenic or non-pathogenic. The microbe may be an infectious agent, such as a clinically important infectious agent. Examples of infectious agents include, but are not limited to bacteria, protozoa, and parasites, and any organism capable of replicating in a host organism, whether extracellularly, intracellularly, or both. See, e.g., G. Kobayashi, Patrick R. Murray, Michael A. Pfaller, and Ken S. Rosenthal; Medical Microbiology, published by Mosby; 4th edition (Jan. 15, 2002), which is incorporated herein by reference in its entirety. A "clinically important infectious agent" is an infectious agent, microbial infectious agent, invading microbe, microbe, bacteria, protozoa, parasite, etc. that causes or is associated with a disease or pathological disorder in an individual.

The term "ex vivo," as used herein, refers to an environment outside of a patient. Accordingly, a sample of bodily fluid collected from a patient is an ex vivo sample of bodily fluid as contemplated by the subject invention.

A "patient", as used herein, refers to an organism, including mammals, from which bodily fluid samples are collected in accordance with the present invention. Mammalian species that benefit from the disclosed systems and methods of detection include, and are not limited to, humans, apes, chimpanzees, orangutans, monkeys; and domesticated animals (e.g., pets) such as dogs, cats, mice, rats, guinea pigs, and hamsters.

"Monitoring" refers to recording changes in a continuously varying parameter, such as growth rate (e.g., doubling time).

A "solid support" (also referred to herein as a "solid substrate") has a fixed organizational support matrix that preferably functions as an organization matrix, such as a microtiter tray. Solid support materials include, but are not limited to, glass, polacryloylmorpholide, silica, controlled pore glass (CPG), polystyrene, polystyrene/latex, polyethylene, polyamide, carboxyl modified teflon, nylon and nitrocellulose and metals and alloys such as gold, platinum and palladium. The solid support can be biological, non-biological, organic, inorganic, or a combination of any of these, existing as particles, strands, precipitates, gels, sheets, tubing, spheres, containers, capillaries, pads, slices, films, plates, slides, etc., depending upon the particular application. Other suitable solid substrate materials will be readily apparent to those of skill in the art. The surface of the solid substrate may contain reactive groups, such as carboxyl, amino, hydroxyl, thiol, or the like for the attachment of nucleic acids, proteins, etc. Surfaces on the solid substrate will sometimes, though not always, be composed of the same material as the substrate. Thus, the surface can be composed of any of a wide variety of materials, for example, polymers, plastics, resins, polysaccharides, silica or silica-based materials, carbon, metals, inorganic glasses, membranes, or any of the above-listed substrate materials.

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state.

As used in this specification, the singular forms "a", "an", and "the" include plural reference unless the context clearly dictates otherwise. Thus, for example, a reference to "a microorganism" includes more than one such microorganism. A reference to "a cell" includes more than one such cell, and so forth.

EXEMPLIFIED EMBODIMENTS

Embodiment 1. A method for determining the specific growth rate of a microbial population, comprising: contacting a non-homogeneous system with at least one protein synthesis inhibitor that inhibits the secondary processing of precursor 16S rRNA but does not inhibit the production of precursor 16S rRNA, wherein the non-homogeneous system potentially comprises a microbial population; obtaining samples from the non-homogeneous system over time following said contacting; and determining the rate of pre16S rRNA accumulation of the microbial population in the samples, if present, wherein the rate of pre16S rRNA accumulation relative to the 16S rRNA is indicative of the specific growth rate.

Embodiment 2. The method of embodiment 1, wherein the at least one protein synthesis inhibitor is selected from the group consisting of chloramphenicol, lincomycin, and erythromycin.

Embodiment 3. The method of embodiment 1 or 2, wherein the determining step comprises contacting the samples with a labeled hybridization probe targeting the precursor 16S rRNA of the microbial population, and detecting a signal from the probe, wherein the signal is indicative of the number of ribosomes present in each sample.

Embodiment 4. The method of embodiment 3, wherein the probe targets the 5' end or 3' end of precursor 16S rRNA.

Embodiment 5. The method of any of embodiments 1-4, wherein the probe targets the interior region of both precursor 16S rRNA and mature 16S rRNA.

Embodiment 6. The method of any of embodiments 1-5, wherein the determining step comprising carrying out fluorescence in situ hybridization (FISH) with an oligonucleotide probe targeting the precursor 16S rRNA of the microbial population.

Embodiment 7. The method of embodiment 6, wherein the probe targets the 5' or 3' end of precursor 16S rRNA.

Embodiment 8. The method of embodiment 6, wherein the probe targets the interior region of both precursor 16S rRNA and mature 16S rRNA.

Embodiment 9. The method of embodiment 1 or 2, wherein the determining step comprises contacting the samples with primers (e.g., pairs, forward and reverse) targeting the precursor 16S rRNA of the microbial population, wherein a detected amplification product is indicative of the number of ribosomes present in each sample.

Embodiment 10. The method of embodiment 9, wherein the primers target the 5' or 3' end of precursor 16S rRNA.

Embodiment 11. The method of embodiment 9, wherein the primers target the interior region of both precursor 16S rRNA and mature 16S rRNA.

Embodiment 12. The method of any of embodiments 1-11, wherein the non-homogeneous system is a mixed cell culture comprising a plurality of distinct microbial populations.

Embodiment 13. The method of any of embodiments 1-11, wherein the non-homogeneous system is water.

Embodiment 14. The method of any of embodiments 1-11, wherein the non-homogeneous system is a biological sample.

Embodiment 15. The method of any of embodiments 1-11, wherein the non-homogeneous system is a bodily fluid.

Embodiment 16. The method of any of embodiments 1-15, wherein the microbial population is bacteria.

Embodiment 17. The method of any of embodiments 1-16, wherein the microbial population is a phosphorus accumulating microorganism.

Embodiment 18. The method of any of embodiments 1-16, wherein the microbial population is nitrifying bacteria.

Embodiment 19. The method of any of embodiments 1-16, wherein the microbial population is a methanogen.

Embodiment 20. The method of any of embodiments 1-16, wherein the microbial population is selected from the group consisting of *Nitrospira* spp., *Nitrosospira* spp., *Nitrobacter* spp., *Nitrosomonas* spp., *Clostridium* spp., *Bacillus* spp., methogenic archaea, coliform, *Salmonella* spp., and *Bacteroides* spp.

Embodiment 21. The method of any of embodiments 1-20, further comprising inputting the rate of pre16S rRNA accumulation of the microbial population into a computer having an algorithm that calculates the specific rate of ribosome synthesis.

Embodiment 22. The method of any of embodiments 1-21, further comprising recording the specific growth rate or specific rate of ribosome synthesis of the microbial population in physical or electronic media.

Embodiment 23. The method of any of embodiments 1-22, further comprising comparing the specific growth rate of the microbial population within the non-homogeneous system with that of a known reference microbial population.

Embodiment 24. A kit for determining the specific growth rate of a microbial population, comprising a compartment containing one or more oligonucleotide probes or primers that target sequence within the precursor 16S rRNA and/or mature 16S rRNA.

Embodiment 25. The kit of embodiment 24, further comprising at least one protein synthesis inhibitor.

Embodiment 26. The kit of embodiment 24, wherein the at least one protein synthesis inhibitor is selected from the group consisting of chloramphenicol, lincomycin, and erythromycin.

Embodiment 27. The kit of any of embodiments 24-26, wherein the probe or primers target the 5' or 3' end of precursor 16S rRNA, or the interior region of both precursor 16S rRNA and mature 16S rRNA.

Embodiment 28. The kit of any of embodiments 24-27, further comprising at least one component selected from the group consisting of a reagent to conduct an amplification reaction, means for obtaining a biological or environmental sample, and a set of instructions relating information regarding components of the kit and/or how to measure specific growth rate of a microbe.

Embodiment 29. The kit of any of embodiments 24-28, further comprising packaging.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification Principles and Practice (2nd ed., Springer-Verlag); and PCR: A Practical Approach (McPherson et al. Eds. (1991) IRL Press)), each of which are incorporated herein by reference in their entirety.

U.S. application Ser. No. 11/521,765, filed Sep. 15, 2006, is incorporated herein by reference in its entirety.

Following is an example that illustrates materials, methods, and procedures for practicing the invention. The example is illustrative and should not be construed as limiting.

Materials and Methods

Model. A simple model was constructed to predict the mathematical relationship between the specific growth rate of a cell and the rate of buildup of pre16S rRNA over time due to chloramphenicol exposure. This model uses empirical data (Table 2) of the ribosome content and cellular volume for *E. coli* cells grown at different specific growth rates (Bremer, H. and P. P. Dennis, "Modulation of chemical composition and other parameters of the cell by growth rate" in *Escherichia coli* and *Salmonella*, F. C. Neidhardt, et al., Editors; 1996, ASM Press: Washington, D.C.). The cell volume is used to convert the ribosome content to ribosome density (ribosomes per cubic micron), which is needed for direct comparison of the FISH data. The mean fluorescent intensity of the cell is a function of pre16S rRNA content and cellular volume (i.e., pre16S rRNA density within the cell).

TABLE 2

Ribosome content and cell size for *E. coli* grown at different specific growth rates.

| Specific growth rate (hr$^{-1}$) | ribosome content (rc) | Size (μm$^3$) |
|---|---|---|
| 0 | N/A | 1 |
| 0.6 | 6,800 | 1 |
| 1.0 | 13,500 | 2 |
| 1.5 | 26,300 | 3 |
| 2.0 | 45,100 | 4 |
| 2.5 | 72,000 | 6 |

The ribosome doubling time (rdt) was determined using the following relationship:

$$rdt = \frac{\ln(2)}{\mu}$$

There is a proportional relationship between mean whole cell fluorescence intensity and the cellular concentration of pre16S rRNA target sites (P) for the FISH probe. The rate of increase in pre16S rRNA (dP/d(rdt)) was calculated by the following equation.

$$\frac{dP}{d(rdt)} = \frac{rc}{rdt}$$

Figure 18:
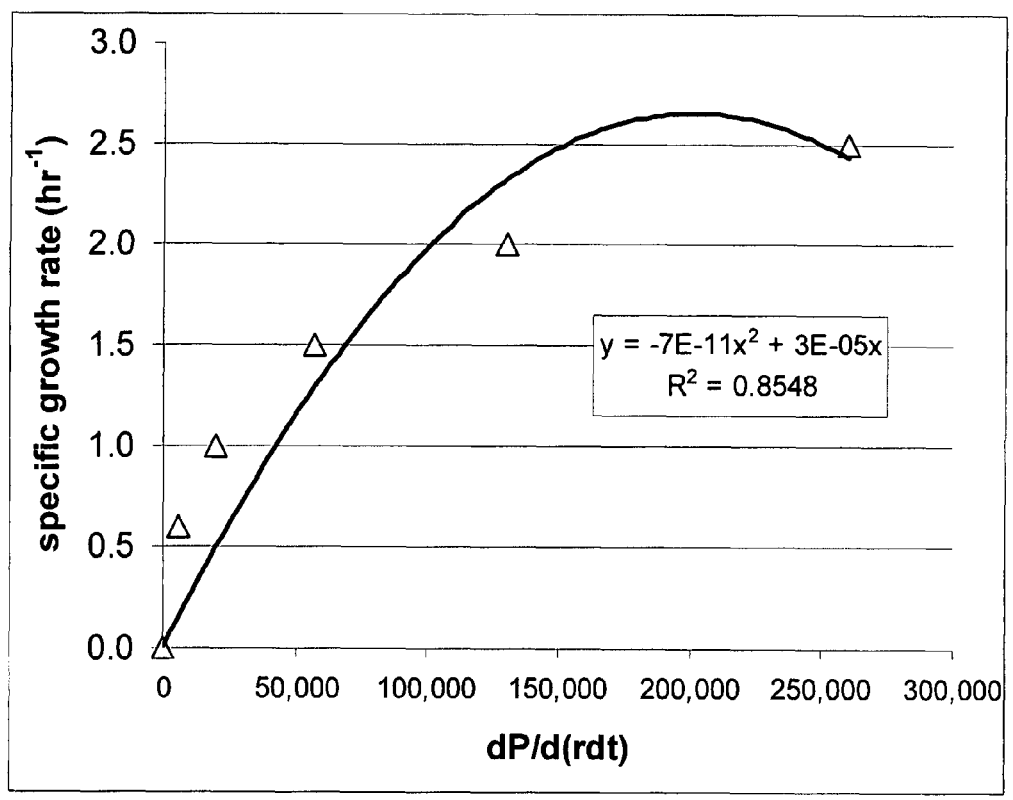
FIG. 18 shows the relationship between specific growth rate and rate of increase of pre16S rRNA (dP/d(rdt)) for $E.$ $coli$ cells.

The pre16S rRNA is represented by the new ribosome content (rc) that is generated for the cell to fully double its ribosomal content in a single rdt. The relationship between the specific growth rate and dP/d(rdt) is shown in FIG. 18. This relationship does not take into consideration the changes in the cell size as a function of the specific growth rate (i.e., the size of cells increases as their specific growth rate increases). In order to determine pre16S rRNA density or concentration in the cell, the pre16S rRNA synthesis rate or dP/d(rdt) was divided by the average cellular volume for each specific growth rate, which is shown in Table 3 and FIG. 19. The $E.$ $coli$ data suggests a strong first or second order relationship between the specific growth rate and dP/d(rdt)–$\mu m^3$.

TABLE 3

Figure 19:
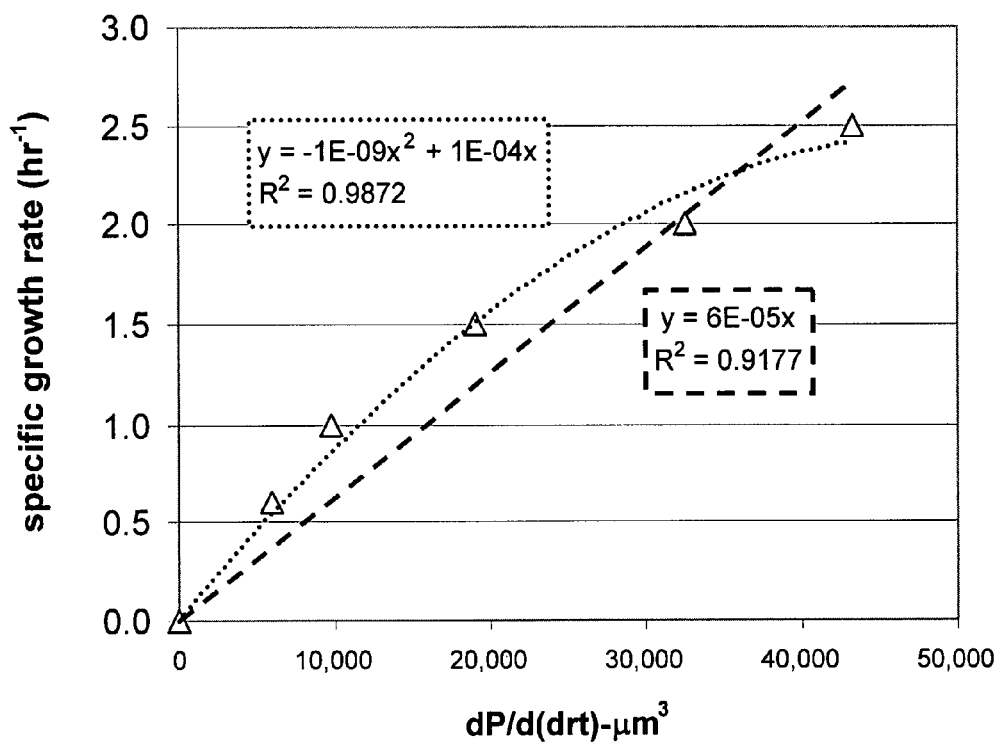
FIG. 19 shows the relationship between specific growth rate and rate of increase of pre16S rRNA buildup corrected for cellular volume (dP/d(drt)–$\mu m^3$) for $E.$ $coli$ cells.

Rate of increase of pre16S rRNA [dP/d(rdt)] and rate of increase of pre16S rRNA buildup corrected for cellular volume [dP/d(rdt) – $\mu m^3$] for $E.$ $coli$ cells at different specific growth rates (FIGS. 18 and 19).

| Specific growth rate (hr$^{-1}$) | dP/d(rdt) | dP/d(rdt) – $\mu m^3$ |
|---|---|---|
| 0 | 0 | 0 |
| 0.6 | 5,886 | 5,886 |
| 1.0 | 19,476 | 9,738 |
| 1.5 | 56,914 | 18,971 |
| 2.0 | 130,131 | 32,533 |
| 2.5 | 259,685 | 43,281 |

Although empirical data is only reported for $E.$ $coli$, it is likely most prokaryotes and single cell eukaryotes will exhibit a similar mathematical relationship. This model predicts a similar relationship (i.e., strong first- or second-order) for the rate of increase of the mean whole cell fluorescence intensity [dF/dt$_{Cm}$] for the fluorescent probe that targets the pre16S rRNA of cells treated with chloramphenicol. To test the model prediction, FISH was conducted with a fluorescent probe that targets the pre16S rRNA of $Acinetobacter$ $calcoaceticus$ and cells were evaluated at different specific growth rates.

Cultures. Four series of samples were investigated using the FISH-RiboSyn approach. Three cultures of $Acinetobacter$ $calcoaceticus$ grown in nutrient broth at 24, 30, and 35° C. and shaken at 200 rpm. The first three series of samples were log growth phase cultures for each temperature, and the fourth series was a stationary phase culture for the 30° C. culture. $Acinetobacter$ $calcoaceticus$ cultures were inoculated from an overnight culture and cultured in a 500 mL culture flask containing 200 mL of nutrient broth (pH 7.2). Each culture was grown in a shaker incubator at 200 rpm and temperature maintained at 24° C., 30° C., or 35° C. This approach would ensure different specific growth rates for each culture, since bacterial growth is sensitive to temperature. The optical density of each culture was measured by a spectrophotometer at 600 nm in order to determine mid-log growth and stationary phases and their respective specific growth rates.

When the culture was in mid-log growth phase (i.e., optical density=~0.40) or stationary phase, 100 mL of the culture was transferred to a sterile flask and subjected to chloramphenicol with a final concentration of 200 mg/L. Samples (2 mL) were collected from this sub-culture every five minutes (including a sample at time zero) for a total of 20 minutes. Each collected sample was immediately centrifuged at 12,205×G for 2 minutes, the supernatant was decanted, and the resulting cell pellet was resuspended in 1 mL of 4% PFA for 12 hours. The samples were centrifuged and supernatant decanted, as previously described, and resuspended in 2 mL of ethanol PBS (Et-PBS). The samples were stored at −20° C. until further analysis by FISH.

A sub-sample of each culture was collected and exposed to chloramphenicol with a final concentration of 200 mg/l. Samples were collected every 5 minutes for 20 minutes and centrifuged at 10,400 rpm for 5 minutes in order to produce cell pellets. Cell pellets were then exposed to a 4% paraformaldehyde solution for a minimum of one hour. Cells were then centrifuged and the supernatant was removed and the cell pellet was resuspended in 1:1 Ethanol:PBS mixture and stored at −20° C.

Fluorescence In Situ Hybridizations (FISH). A fluorescently-labeled oligonucleotide hybridization probe targeting the precursor 16S rRNA for the members of the genus $Acinetobacter$ (Acin1543; 5' GATTCTTACCAATCGT-CAATCTTT 3' (SEQ ID NO:2)) (Oerther, D. B. et al. $App$ $Environ Microbiol,$ 2000, 66(5):2154-2165) was synthesized and conjugated with the cyanine dye, Cy3, before purification with oligonucleotide probe purification cartridges. Fluorescently labeled probes were diluted to 50 ng/µL with H$_2$O, and stored in 50-µL aliquots at −20° C. in the dark.

Fixed samples were applied in a sample well on a Heavy Teflon Coated microscope slide (Cel-Line Associates, New Field, N.J.) and air-dried. After dehydration with an increasing ethanol series (50, 80, 95% [vol/vol] ethanol, 1 min each), each sample well was covered with 9 µL of hybridization buffer (20% [vol/vol] formamide, 0.9 M NaCl, 100 mM Tris HCl [pH 7.0], 0.1% SDS) (de los Reyes, F. L. et al. $App$ $Environ Microbiol,$ 1997, 63:1107-1117). Fluorescently labeled oligonucleotide probe, 1 µL (50 ng), was added to each well of the microscope slide and hybridizations were conducted in a moisture chamber for 1 h, in the dark, at 46° C. The slides were washed for 30 min at 48° C. with 50 mL of prewarmed wash solution (215 mM NaCl, 20 mM Tris HCl [pH 7.0], 0.1% SDS, and 5 mM EDTA) (de los Reyes, F. L. et al. $App Environ Microbiol,$ 1997, 63:1107-1117). Hybridized cells were stained with 100 µl/well of DAPI solution (1 µg/ml) for one minute and slides were stored at −20° C. Fixed, hybridized cells were mounted with Cargille immersion oil (Type FF, Cedar Grove, N.J.) and a cover slip.

DAPI and probe conferred fluorescence were visualized with an upright epifluorescence microscope (Leitz DiaPlan, Heerbrugg, Switzerland), and digital images were captured using a Spot-FLEX charge coupled device (CCD) camera (Diagnostic Instruments, Inc., Sterling Heights, Mich.). All FISH images were collected with the same camera settings of exposure time=1.1 sec and gain=1.

FISH Digital Image Analysis. The digital images of each FISH series were evaluated with the Daime software package (Daims, H. et al. $Environ Microbiol,$ 2006, 8(2):200-213). Images were automatically segmented (2D segmentation mode, Thresholding Biomass detection, Associative map object detection, and RATS thresholding algorithm). The "Measure objects" function was used to determine the number of objects detected, as well as the mean fluorescence intensity and standard deviation of the fluorescence intensity of each object.

EXAMPLE 1

Figures 10A, 10B, 10C, 10D, 10E, 10F:
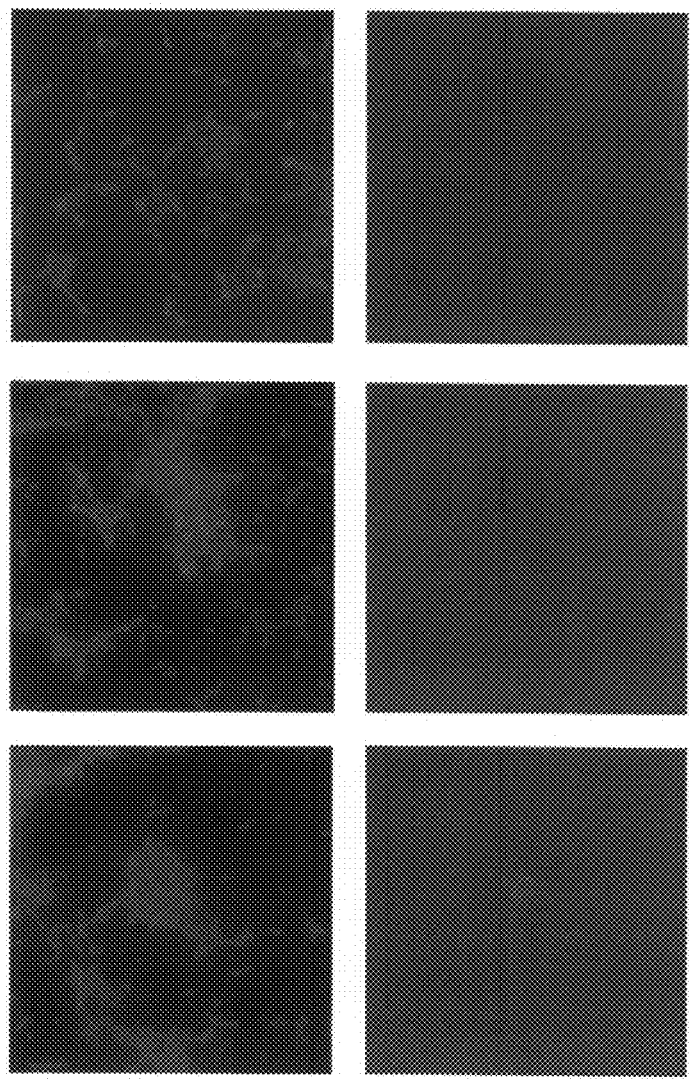
FIGS. 10A-10F show 1000× DAPI and FISH images of a stationary phase culture of $A.$ $calcoaceticus$ incubated at 30° C. with a specific growth rate of 0 $hr^{-1}$ exposed to chloramphenicol for 0 minutes (DAPI.
Figure 11A:
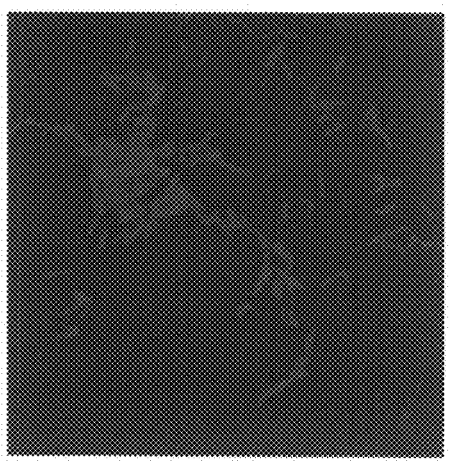
FIGS. 11A-11C show 1000× FISH images of a log phase culture of $A.$ $calcoaceticus$ incubated at 24° C. with an 89 min doubling time or specific growth rate of 0.47 $hr^{-1}$ exposed to chloramphenicol for 0 minutes (FIG. 11A), 10 minutes (FIG. 11B), and 20 minutes (FIG. 11C).
Figure 11B:
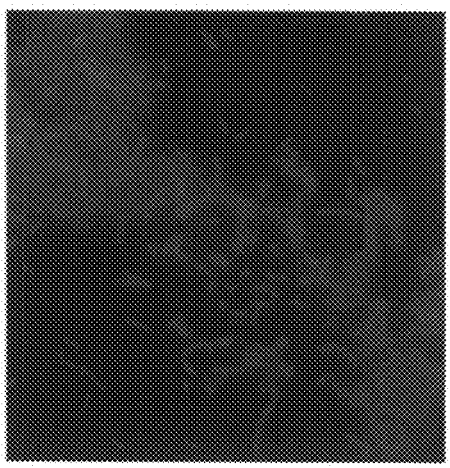
Figure 11C:
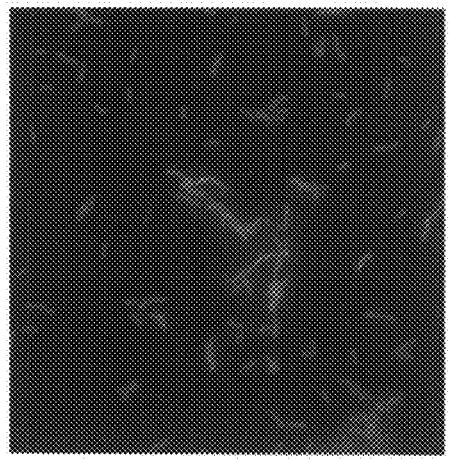
Figure 12A:
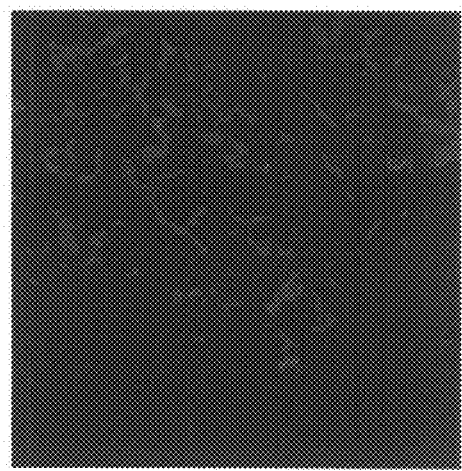
FIGS. 12A-12C show 1000× FISH images of a log phase culture of $A.$ $calcoaceticus$ incubated at 35° C. with an 74 min doubling time or specific growth rate of 0.56 $hr^{-1}$ exposed to chloramphenicol for 0 minutes (FIG. 12A), 10 minutes (FIG. 12B), and 20 minutes (FIG. 12C).
Figure 12B:
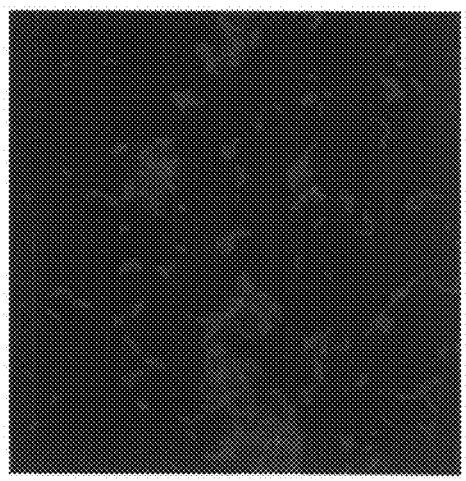
Figure 12C:
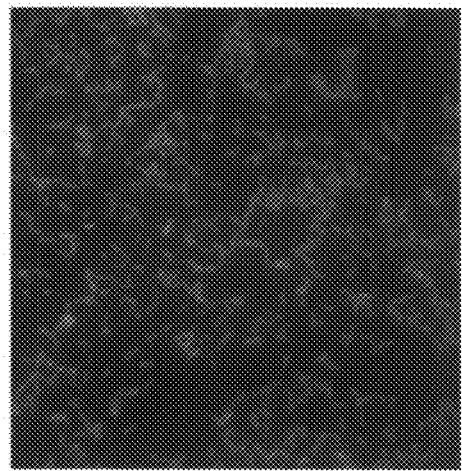
Figure 13C:
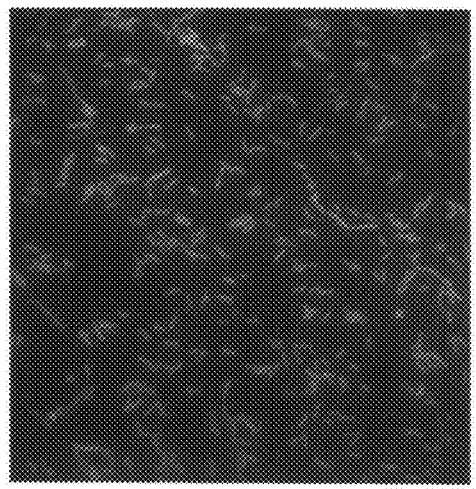
FIGS. 13A-13C show 1000× FISH images of a log phase culture of $A.$ $calcoaceticus$ incubated at 30° C. with an 63 min doubling time or specific growth rate of 0.66 $hr^{-1}$ exposed to chloramphenicol for 0 minutes (FIG. 13A), 10 minutes (FIG. 13B), and 20 minutes (FIG. 13C).
Figure 13B:
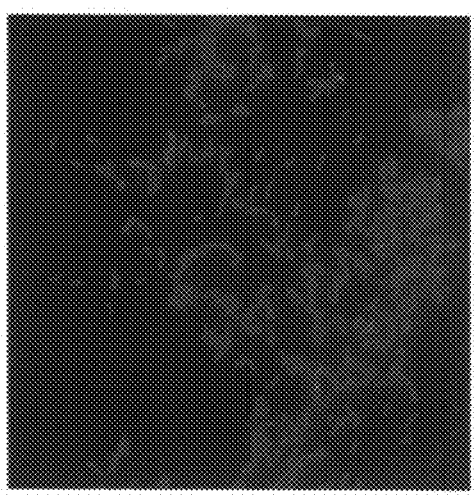
Figure 13A:
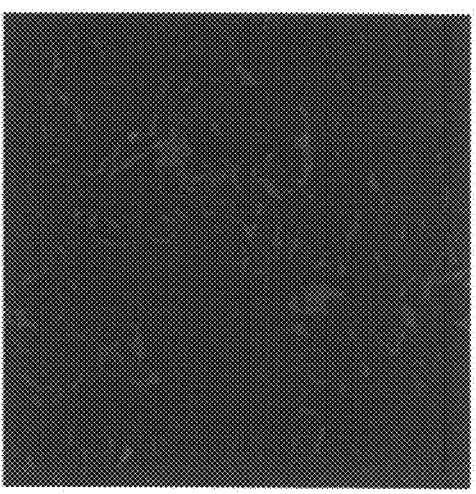

FISH Results Demonstrate a Strong Linear Relationship Between the dF/dt$_{Cm}$ and Specific Growth Rate for *A. calcoaceticus* Cultured at Four Different Specific Growth Rates The experimental results described below provide evidence that the FISH-RiboSyn method can be used to measure the dF/dt$_{Cm}$, which is directly related to the specific growth rate. In FIGS. 10A-10F, 11A-11C, 12A-12C, and 13A-13C, DAPI and FISH images are shown for the chloramphenicol-treated cultures of *A. calcoaceticus*. For the stationary phase culture (FIGS. 10A-10F), DAPI images (FIGS. 10A-C) reveal several bacteria cells, but the FISH images (FIGS. 10D-F) provide evidence that the chloramphenicol-treated cells did not accumulate pre16S rRNA because ribosome synthesis has ceased, which results in cells with low and constant fluorescent intensity. However, chloramphenicol-treated cells from the log growth cultures (FIGS. 11A-11C, 12A-12C, and 13A-13C) have active ribosome synthesis, which results in the accumulation of pre16S rRNA and the fluorescent intensity of the cells increase with longer exposure to chloramphenicol.

The digital images of each FISH series were evaluated and the mean fluorescence intensity and standard deviation of the fluorescence intensity of each object are provided in Table 4. The high standard deviation is typical of images collected by the use of an epifluorescence microscope system. There is a clear difference between the three FISH image series (Tables 4, 5, 6, and 7 and FIGS. 10D-10F, 11A-10C, 12A-12C, and 13A-13C).

TABLE 4

Digital image analysis of samples collected at various times of chloramphenicol exposure for *A. calcoaceticus* grown at 30° C. with a specific growth rate of 0.00 hr$^{-1}$.

| time | mean | std dev | Thresholding high | Thresholding low | objects | COV |
|---|---|---|---|---|---|---|
| 0 | 4.2 | 0.6 | 255 | 4 | 382 | 14.29% |
| 5 | 4.4 | 0.6 | 255 | 4 | 327 | 13.64% |
| 10 | 4.2 | 0.5 | 255 | 4 | 363 | 11.90% |
| 15 | 4.2 | 0.6 | 255 | 4 | 348 | 14.29% |
| 20 | 4.2 | 0.5 | 255 | 4 | 474 | 11.90% |

TABLE 5

Digital image analysis of samples collected at various times of chloramphenicol exposure for *A. calcoaceticus* grown at 24° C. with a specific growth rate of 0.47 hr$^{-1}$.

| time | mean | std dev | Thresholding high | Thresholding low | objects | COV |
|---|---|---|---|---|---|---|
| 0 | 30.5 | 3.6 | 255 | 25 | 519 | 11.80% |
| 5 | 41.1 | 5.7 | 255 | 33 | 383 | 13.87% |
| 10 | 50.2 | 6.1 | 255 | 42 | 407 | 12.15% |
| 15 | 64.6 | 9.5 | 255 | 51 | 362 | 14.71% |
| 20 | 77.3 | 11.3 | 255 | 56 | 585 | 14.62% |

TABLE 6

Digital image analysis of samples collected at various times of chloramphenicol exposure for *A. calcoaceticus* grown at 35° C. with a specific growth rate of 0.56 hr$^{-1}$.

| time | mean | std dev | Thresholding high | Thresholding low | objects | COV |
|---|---|---|---|---|---|---|
| 0 | 31.5 | 5.7 | 250 | 25 | 425 | 18.10% |
| 5 | 37.2 | 4.7 | 255 | 30 | 499 | 12.63% |
| 10 | 55.2 | 5.8 | 255 | 46 | 444 | 10.51% |
| 15 | 68 | 9.8 | 255 | 52 | 734 | 14.41% |
| 20 | 82.5 | 12.6 | 255 | 60 | 736 | 15.27% |

TABLE 7

Digital image analysis of samples collected at various times of chloramphenicol exposure for *A. calcoaceticus* grown at 30° C. with a specific growth rate of 0.66 hr$^{-1}$.

| time | mean | std dev | Thresholding high | Thresholding low | objects | COV |
|---|---|---|---|---|---|---|
| 0 | 30.3 | 4.4 | 228 | 25 | 428 | 14.52% |
| 5 | 41.7 | 4.9 | 255 | 39 | 832 | 11.75% |
| 10 | 55.3 | 6.7 | 255 | 46 | 455 | 12.12% |
| 15 | 65.1 | 8.3 | 255 | 52 | 466 | 12.75% |
| 20 | 99.1 | 17.2 | 252 | 67 | 901 | 17.36% |

Figure 14:
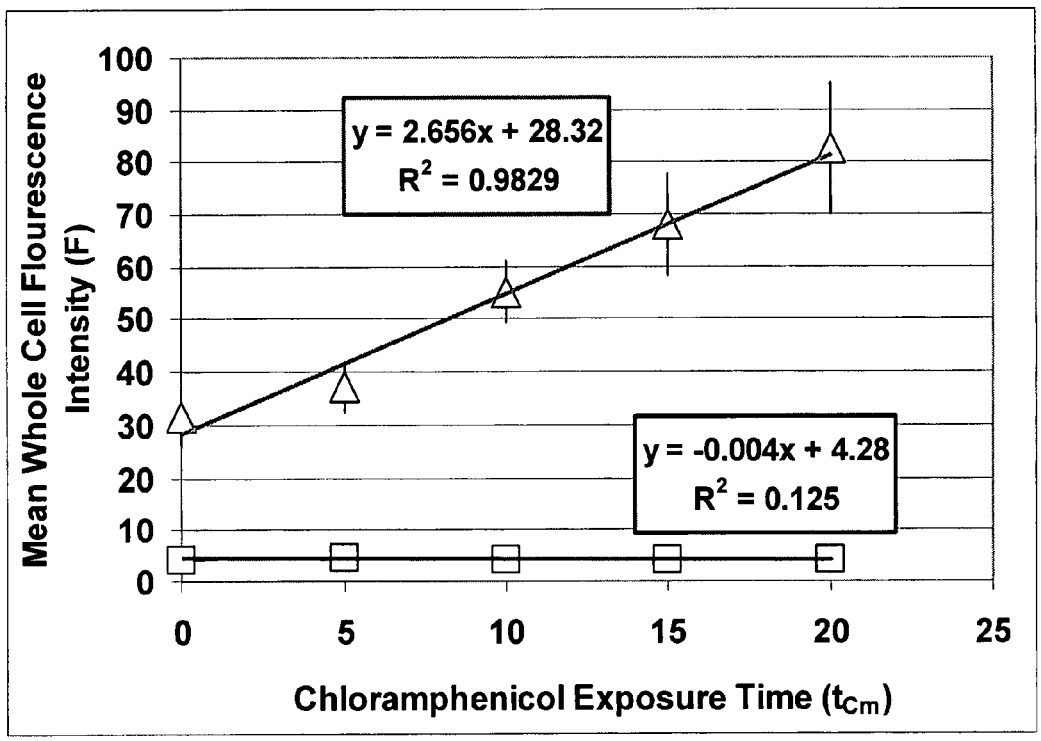
FIG. 14 shows mean whole cell fluorescence intensity over time for two series of FISH images corresponding to a log growth phase and stationary phase $A.$ $calcoaceticus$ culture exposed to chloramphenicol at various times.

For each culture, the mean whole cell fluorescence intensity for the series of samples (Tables 4-7) was plotted as a function of chloramphenicol exposure time. The linear regression function of Microsoft Excel was used to analyze the data and determine the slope, which is the dF/dt$_{Cm}$. Examples of these linear regressions are shown graphically in FIG. 14 for the 35° C. culture and the stationary phase culture. The slope of these linear regressions is the dF/dt$_{Cm}$ and is provided in Table 8. Good agreement (i.e., high $R^2$ value) was determined for the data set of each culture with cells in log growth.

TABLE 8

The dF/dt$_{Cm}$ of the four *A. calcoaceticus* cultures at distinct specific growth rates.

| Culture | μ (hr$^{-1}$) | dF/dt$_{Cm}$ | $R^2$ |
|---|---|---|---|
| 30° C. | 0.660 | 3.22 | 0.9326 |
| 35° C. | 0.562 | 2.656 | 0.9829 |
| 24° C. | 0.467 | 2.342 | 0.9934 |
| stationary phase | 0.000 | −0.004 | 0.1250 |

Figure 15:
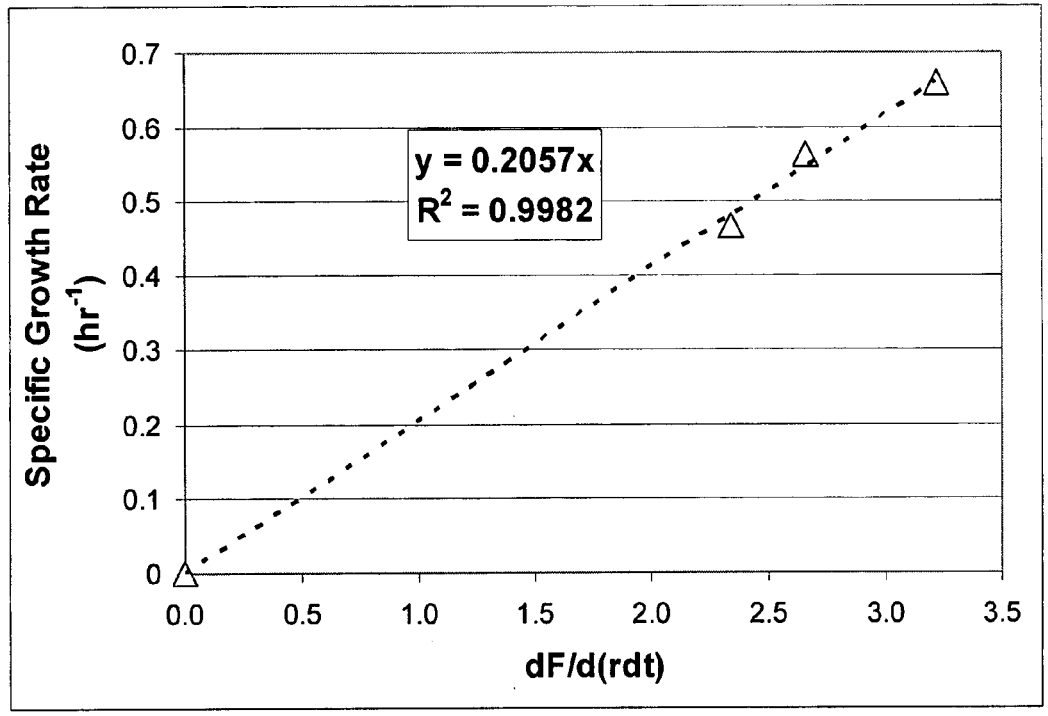
FIG. 15 shows the first and second order relationship between the specific growth rate ($\mu$) and the rate of increase of the whole cell mean fluorescence intensity over time [dF/$dt_{Cm}$] of $A.$ $calcoaceticus$ cultures exposed to chloramphenicol.
Figure 16:
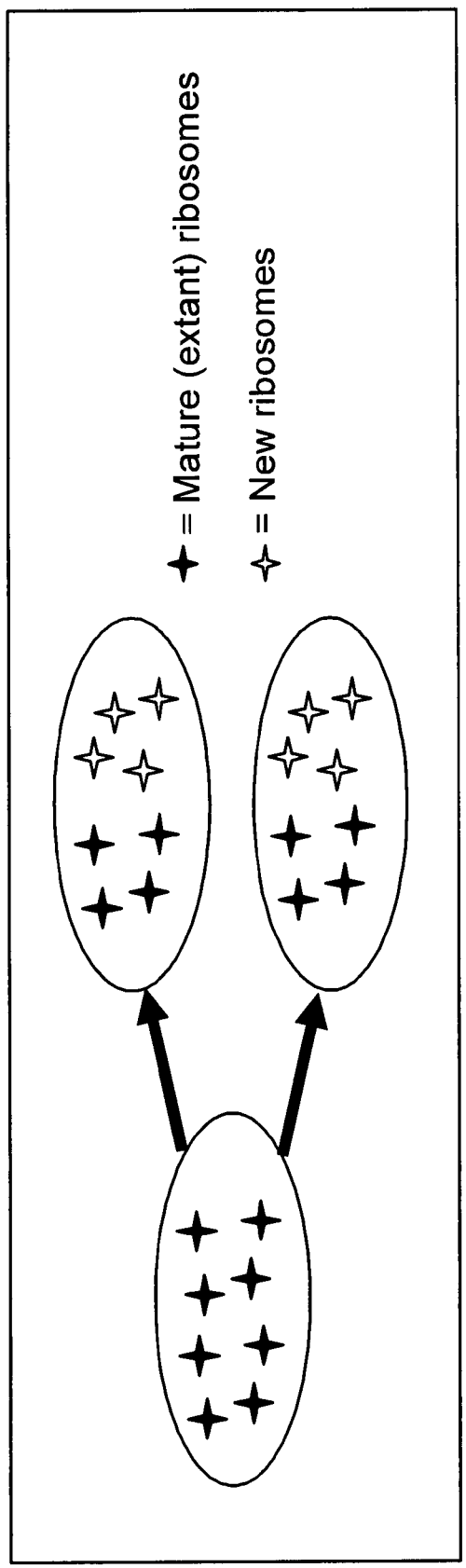
FIG. 16 shows normal ribosome synthesis and how it relates to cell doubling.
Figure 17:
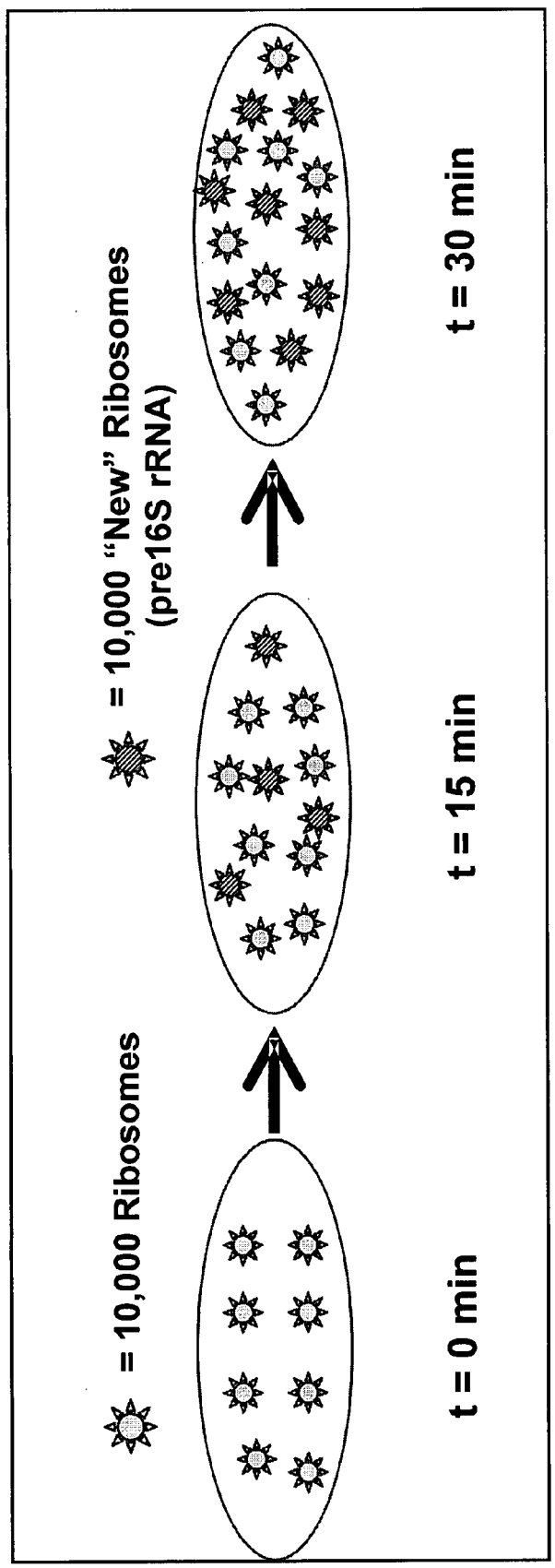
FIG. 17 shows rate of accumulation of pre16S rRNA at t=0 minutes, t=15 minutes, and t=30 minutes following protein synthesis inhibition (chloramphenicol exposure), which prevents cell doubling.

The relationship between the specific growth rate of the four *A. calcoaceticus* cultures and the dF/dt$_{Cm}$ is shown in FIG. 15. A strong linear relationship ($R^2$=0.9982) was determined between the specific growth rate and dF/dt$_{Cm}$, which is in agreement with the predictions of the model described herein. Furthermore, FIG. 15 demonstrates that a standard curve can be determined for the specific growth rate of a distinct microbial population and the dF/dt$_{Cm}$, which can then be used to measure the specific growth rate of the distinct microbial population in a sample of interest.

All patents, patent applications, provisional applications, and publications referred to or cited herein are incorporated by reference in their entirety, including all figures and tables, to the extent they are not inconsistent with the explicit teachings of this specification.

It should be understood that the example and embodiments described herein are for illustrative purposes only and that various modifications or changes in light thereof will be suggested to persons skilled in the art and are to be included within the spirit and purview of this application.

7. The method of claim 6, wherein the probe targets the 5' or 3' end of precursor 16S rRNA.

8. The method of claim 6, wherein the probe targets the interior region of both precursor 16S rRNA and mature 16S rRNA.

We claim:

1. A method for determining the specific growth rate of a microbial population, comprising:
    contacting a non-homogeneous system with at least one protein synthesis inhibitor that inhibits the secondary processing of precursor 16S rRNA but does not inhibit the production of precursor 16S rRNA, wherein the non-homogeneous system potentially comprises a microbial population;
    obtaining samples from the non-homogeneous system over time following said contacting; and
    determining the rate of precursor 16S rRNA accumulation of the microbial population in the samples, if present, wherein the rate of precursor 16S rRNA accumulation relative to the 16S rRNA is indicative of the specific growth rate of the microbial population.

2. The method of claim 1, wherein the at least one protein synthesis inhibitor is selected from the group consisting of chloramphenicol, lincomycin, and erythromycin.

3. The method of claim 1, wherein said determining comprises contacting the samples with a labeled hybridization probe targeting the precursor 16S rRNA of the microbial population, and detecting a signal from the probe, wherein the signal is indicative of the number of ribosomes present in each sample.

4. The method of claim 3, wherein the probe targets the 5' end or 3' end of precursor 16S rRNA.

5. The method of claim 3, wherein the probe targets the interior region of both precursor 16S rRNA and mature 16S rRNA.

6. The method of claim 1, wherein said determining comprises conducting carrying out fluorescence in situ hybridization (FISH) with an oligonucleotide probe targeting the precursor 16S rRNA of the microbial population.

9. The method of claim 1, wherein said determining comprises contacting the samples with primers targeting the precursor 16S rRNA of the microbial population for amplification, wherein the production of an amplification product from said amplification is indicative of the number of ribosomes present in each sample.

10. The method of claim 1, wherein the non-homogeneous system is a mixed cell culture comprising a plurality of distinct microbial populations.

11. The method of claim 1, wherein the non-homogeneous system is water.

12. The method of claim 1, wherein the non-homogeneous system is a biological sample.

13. The method of claim 1, wherein the non-homogeneous system is a bodily fluid.

14. The method of claim 1, wherein the microbial population is bacteria.

15. The method of claim 1, wherein the microbial population is a phosphorus accumulating microorganism.

16. The method of claim 1, wherein the microbial population is nitrifying bacteria.

17. The method of claim 1, wherein the microbial population is a methanogen.

18. The method of claim 1, wherein the microbial population is selected from the group consisting of *Nitrospira* spp., *Nitrosospira* spp., *Nitrobacter* spp., *Nitrosomonas* spp., *Clostridium* spp., *Bacillus* spp., methogenic archaea, coliform, *Salmonella* spp., and *Bacteroides* spp.

19. The method of claim 1, further comprising inputting the rate of precursor 16S rRNA accumulation of the microbial population into a computer algorithm that calculates the specific rate of ribosome synthesis.

20. The method of claim 1, further comprising recording the specific growth rate or specific rate of ribosome synthesis of the microbial population in physical or electronic media.

21. The method of claim 1, further comprising comparing the specific growth rate of the microbial population within the non-homogeneous system with that of a known reference microbial population.

* * * * *

UNITED STATES PATENT AND TRADEMARK OFFICE
CERTIFICATE OF CORRECTION

PATENT NO. : 7,771,941 B2
APPLICATION NO. : 11/821946
DATED : August 10, 2010
INVENTOR(S) : Peter George Stroot et al.

It is certified that error appears in the above-identified patent and that said Letters Patent is hereby corrected as shown below:

Column 3,
Line 61, "Table I" should read --Table 1--.

Column 25,
Line 36, "11A-10C" should read --11A-11C--.

Signed and Sealed this
Fourth Day of January, 2011

David J. Kappos
*Director of the United States Patent and Trademark Office*

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: oligonucleotide probe

<400> SEQUENCE: 1
ggtttcccgt tccatctt                                                18

<210> SEQ ID NO 2
<211> LENGTH: 24
<212> TYPE: DNA
<213> ORGANISM: Artificial Sequence
<220> FEATURE:
<223> OTHER INFORMATION: oligonucleotide probe

<400> SEQUENCE: 2
gattcttacc aatcgtcaat cttt                                         24